(12) United States Patent
Appling et al.

(10) Patent No.: US 8,585,950 B2
(45) Date of Patent: Nov. 19, 2013

(54) MULTILUMEN CATHETERS AND METHOD OF MANUFACTURING

(75) Inventors: William M. Appling, Granville, NY (US); Theodore J. Beyer, Queensbury, NY (US); Carol L. Lancette, Hudson Falls, NY (US)

(73) Assignee: AngioDynamics, Inc., Latham, NY (US)

( * ) Notice: Subject to any disclaimer, the term of this patent is extended or adjusted under 35 U.S.C. 154(b) by 417 days.

(21) Appl. No.: 12/648,153

(22) Filed: Dec. 28, 2009

(65) Prior Publication Data

US 2010/0191165 A1    Jul. 29, 2010

Related U.S. Application Data

(60) Provisional application No. 61/148,078, filed on Jan. 29, 2009.

(51) Int. Cl.
*B31B 37/00* (2006.01)

(52) U.S. Cl.
USPC .......................................... 264/248; 604/523

(58) Field of Classification Search
USPC ............................ 264/248; 604/264, 284, 523
See application file for complete search history.

(56) References Cited

U.S. PATENT DOCUMENTS

| | | |
|---|---|---|
| 2,122,335 A | 6/1938 | Berman et al. |
| 3,380,229 A | 4/1968 | Nelson |
| 3,440,118 A | 4/1969 | Obeda |
| 3,537,935 A | 11/1970 | Withers |
| 3,586,555 A | 6/1971 | Sager |
| 3,897,296 A | 7/1975 | Waldrum |
| 4,795,439 A * | 1/1989 | Guest .............................. 604/43 |
| 4,838,881 A | 6/1989 | Bennett |
| 4,923,659 A | 5/1990 | Kunz |
| 4,978,408 A | 12/1990 | Burford et al. |
| 5,135,599 A | 8/1992 | Martin et al. |
| 5,137,671 A | 8/1992 | Conway et al. |
| 5,156,592 A | 10/1992 | Martin et al. |
| 5,178,803 A | 1/1993 | Tsuchida et al. |
| 5,180,372 A | 1/1993 | Vegoe et al. |
| 5,195,962 A | 3/1993 | Martin et al. |

(Continued)

FOREIGN PATENT DOCUMENTS

| | | |
|---|---|---|
| CN | 2002-0083424 | 11/2002 |
| EP | 0747077 | 12/1996 |

(Continued)

OTHER PUBLICATIONS

Ash, Advances in Tunneled Central Venous Catheters for Dialysis: Design and Performance, Seminars in Dialysis, p. 1-12 (2008).

(Continued)

*Primary Examiner* — Galen Hauth
(74) *Attorney, Agent, or Firm* — Ryan D. Artis

(57) ABSTRACT

A multilumen catheter assembly and method of making the catheter assembly is provided that involves providing a plurality of tubes, each tube having a first end, a second end, at least one lumen, and at least one surface, selectively heating at least a portion of the surface of at least a first tube of the plurality of tubes, and contacting the selectively heated portion of the tube with a portion of the surface of a second tube to form a multilumen catheter shaft that is joined together along at least a portion of the length of the catheter shaft.

29 Claims, 13 Drawing Sheets

(56) References Cited

U.S. PATENT DOCUMENTS

| | | | |
|---|---|---|---|
| 5,215,614 A | 6/1993 | Wijkamp et al. |
| 5,221,256 A | 6/1993 | Mahurkar |
| 5,240,537 A | 8/1993 | Bodicky |
| 5,348,536 A | 9/1994 | Young et al. |
| 5,374,245 A | 12/1994 | Mahurkar |
| 5,397,418 A | 3/1995 | Shimizu et al. |
| 5,403,291 A | 4/1995 | Abrahamson |
| 5,421,832 A | 6/1995 | Lefebvre |
| 5,451,206 A | 9/1995 | Young et al. |
| 5,464,398 A | 11/1995 | Haindl |
| 5,469,915 A | 11/1995 | Cesaroni |
| 5,472,417 A | 12/1995 | Martin et al. |
| 5,484,565 A | 1/1996 | Larsen et al. |
| 5,486,159 A | 1/1996 | Mahurkar |
| 5,489,278 A | 2/1996 | Abrahamson |
| 5,509,897 A | 4/1996 | Twardowski et al. |
| 5,533,985 A | 7/1996 | Wang |
| 5,547,364 A | 8/1996 | Wong et al. |
| 5,549,580 A | 8/1996 | Diaz |
| 5,558,737 A | 9/1996 | Brown et al. |
| 5,630,794 A | 5/1997 | Lax et al. |
| 5,693,416 A | 12/1997 | Kucherovsky |
| 5,711,909 A | 1/1998 | Gore et al. |
| 5,713,851 A | 2/1998 | Boudewijn |
| 5,730,741 A | 3/1998 | Horzewski et al. |
| 5,736,094 A | 4/1998 | van Muiden |
| 5,738,666 A | 4/1998 | Watson et al. |
| 5,738,742 A | 4/1998 | Stevens |
| 5,766,151 A * | 6/1998 | Valley et al. ............ 604/103.07 |
| 5,769,830 A | 6/1998 | Parker |
| 5,807,311 A | 9/1998 | Palestrant |
| 5,830,401 A | 11/1998 | Prichard et al. |
| 5,879,499 A | 3/1999 | Corvi |
| 5,902,247 A | 5/1999 | Coe et al. |
| 5,947,953 A | 9/1999 | Ash et al. |
| 5,951,929 A | 9/1999 | Wilson |
| 6,001,079 A | 12/1999 | Pourchez |
| 6,030,371 A | 2/2000 | Pursley |
| 6,078,830 A | 6/2000 | Levin et al. |
| 6,139,525 A | 10/2000 | Davis-Lemessy et al. |
| 6,146,354 A | 11/2000 | Beil |
| 6,156,016 A | 12/2000 | Maginot |
| 6,190,349 B1 | 2/2001 | Ash et al. |
| 6,264,679 B1 | 7/2001 | Keller et al. |
| 6,280,788 B1 | 8/2001 | Rakhorst et al. |
| 6,503,353 B1 | 1/2003 | Peterson et al. |
| 6,511,462 B1 | 1/2003 | Itou et al. |
| 6,524,302 B2 * | 2/2003 | Kelley ............... 604/523 |
| 6,632,315 B2 | 10/2003 | Liska et al. |
| 6,695,832 B2 | 2/2004 | Schon et al. |
| 6,719,749 B1 | 4/2004 | Schweikert et al. |
| 6,743,218 B2 | 6/2004 | Maginot et al. |
| 6,758,836 B2 | 7/2004 | Zawacki |
| 6,817,632 B1 | 11/2004 | You et al. |
| 6,827,798 B1 | 12/2004 | Ichikawa et al. |
| 6,858,019 B2 | 2/2005 | McGuckin et al. |
| 6,881,211 B2 | 4/2005 | Schweikert et al. |
| 6,916,313 B2 | 7/2005 | Cunningham |
| 7,018,374 B2 | 3/2006 | Schon et al. |
| 7,069,634 B1 | 7/2006 | Elsberry |
| 7,223,254 B2 | 5/2007 | Hjalmarsson |
| 7,331,948 B2 | 2/2008 | Skarda |
| 7,393,339 B2 | 7/2008 | Zawacki et al. |
| RE40,913 E | 9/2009 | Schweikert et al. |
| 2002/0029994 A1 | 3/2002 | Schon |
| 2003/0153898 A1 | 8/2003 | Schon et al. |
| 2003/0201059 A1 * | 10/2003 | Holman et al. ............... 156/155 |
| 2004/0059314 A1 | 3/2004 | Schon et al. |
| 2004/0087892 A1 | 5/2004 | Cunningham |
| 2004/0092863 A1 | 5/2004 | Raulerson et al. |
| 2004/0167463 A1 | 8/2004 | Zawacki et al. |
| 2004/0243095 A1 | 12/2004 | Nimkar et al. |
| 2005/0033222 A1 | 2/2005 | Haggstrom et al. |
| 2005/0054990 A1 | 3/2005 | Graft et al. |
| 2005/0055012 A1 | 3/2005 | Trerotola |
| 2005/0096585 A1 | 5/2005 | Schon et al. |
| 2005/0119616 A1 | 6/2005 | Goodin et al. |
| 2005/0277862 A1 | 12/2005 | Anand |
| 2006/0161100 A1 * | 7/2006 | Hamboly ............... 604/43 |
| 2007/0225661 A1 | 9/2007 | Ash et al. |
| 2008/0009803 A1 | 1/2008 | Schon et al. |
| 2008/0039774 A1 | 2/2008 | Zawacki et al. |
| 2008/0188802 A1 | 8/2008 | Shah |
| 2008/0214980 A1 | 9/2008 | Anand |
| 2009/0054826 A1 | 2/2009 | Hoffa |
| 2009/0069792 A1 | 3/2009 | Frey et al. |
| 2009/0112153 A1 | 4/2009 | Gregersen et al. |
| 2009/0118661 A1 | 5/2009 | Moehle et al. |
| 2009/0137944 A1 | 5/2009 | Haarala et al. |
| 2009/0157052 A1 | 6/2009 | Verbitsky et al. |
| 2009/0165881 A1 | 7/2009 | Tegg et al. |
| 2009/0166913 A1 | 7/2009 | Guo et al. |
| 2009/0204052 A1 | 8/2009 | Nimkar et al. |
| 2009/0204079 A1 | 8/2009 | Nimkar et al. |
| 2009/0205189 A1 | 8/2009 | Nimkar et al. |
| 2009/0209940 A1 | 8/2009 | Nimkar et al. |

FOREIGN PATENT DOCUMENTS

| | | |
|---|---|---|
| EP | 1252910 B1 | 9/2007 |
| JP | 2006-285165 | 6/1994 |
| JP | 2002-331036 | 11/2002 |
| JP | 2006-102537 | 4/2006 |
| JP | 2007-40377 | 2/2007 |
| JP | 2007-307875 | 11/2007 |

OTHER PUBLICATIONS

Fry et al., Factors Affecting Long-term Survival of Tunnelled Haemodialysis Catheters—a Prospective Audit of 812 Tunnelled Catheters, Nephrol Dial Transplant, p. 1-7 (2007).

Smith et al., Transhepatic Catheter Access for Hemodialysis, Radiology, 232:246-251 (2004).

Trerotola, Hemodialysis Catheter Placement and Management, Radiology, 215:651-658 (2000).

Vesely, Chronic Hemodialysis Catheters, Endovascular Today, p. 27-28 (Aug. 2005).

Forward Technology, Plastic Assembly—Hot Plate Welders, http://www.forwardtech.com/PlasticAssembly/HotPlate.

U.S. Appl. No. 12/648,169, filed Dec. 28, 2009.

Tool and Manufacturing Engineers Handbook, vol. 8, Plastic Part Manufacturing, 4th Ed., p. 16-26, Copyright 1996.

* cited by examiner

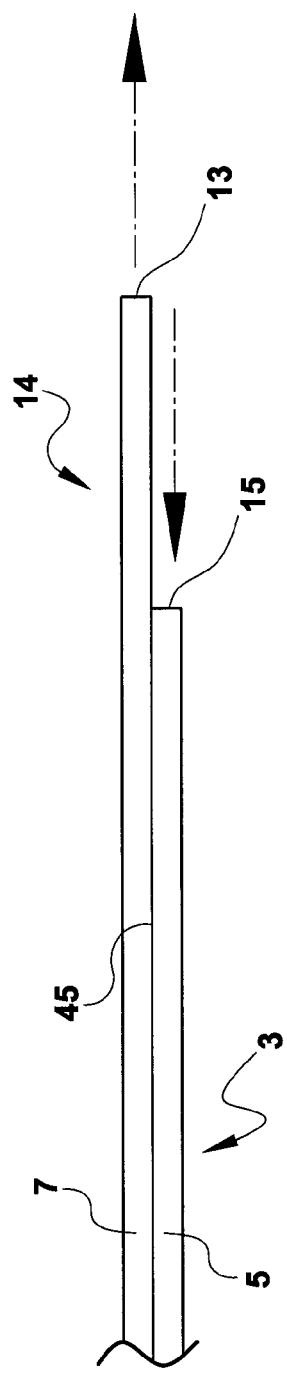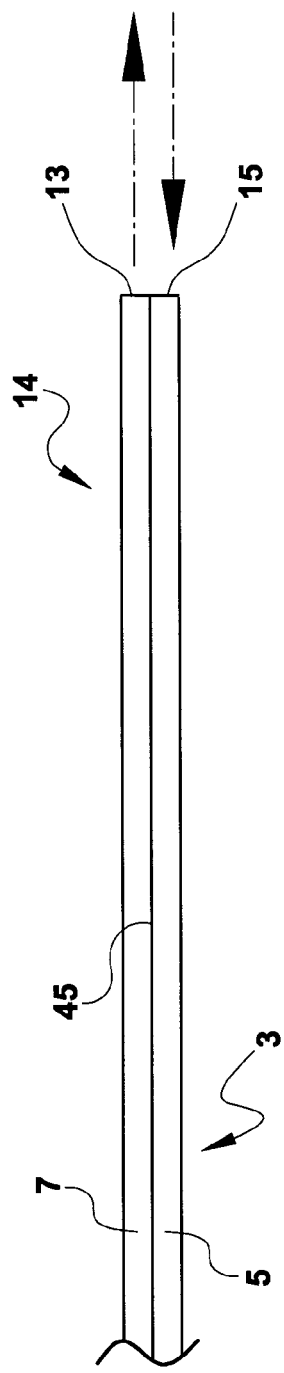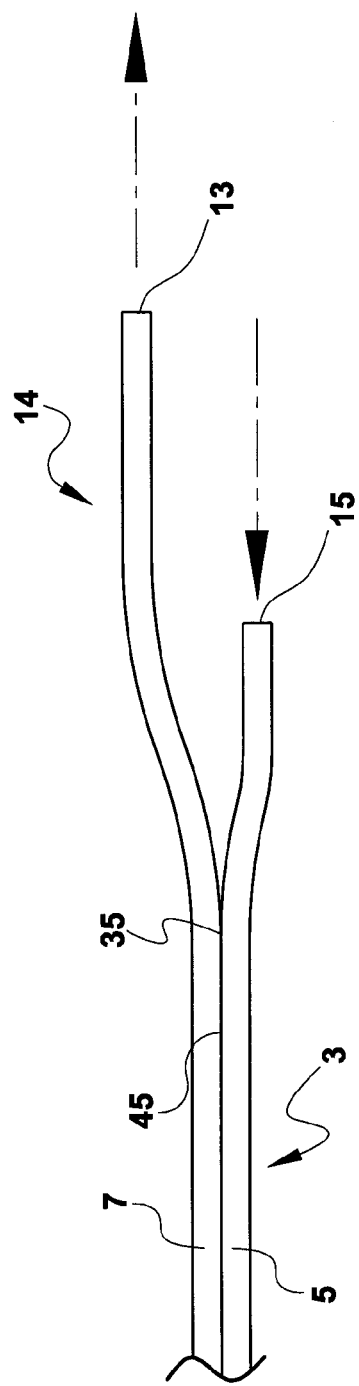

FIG. 6A
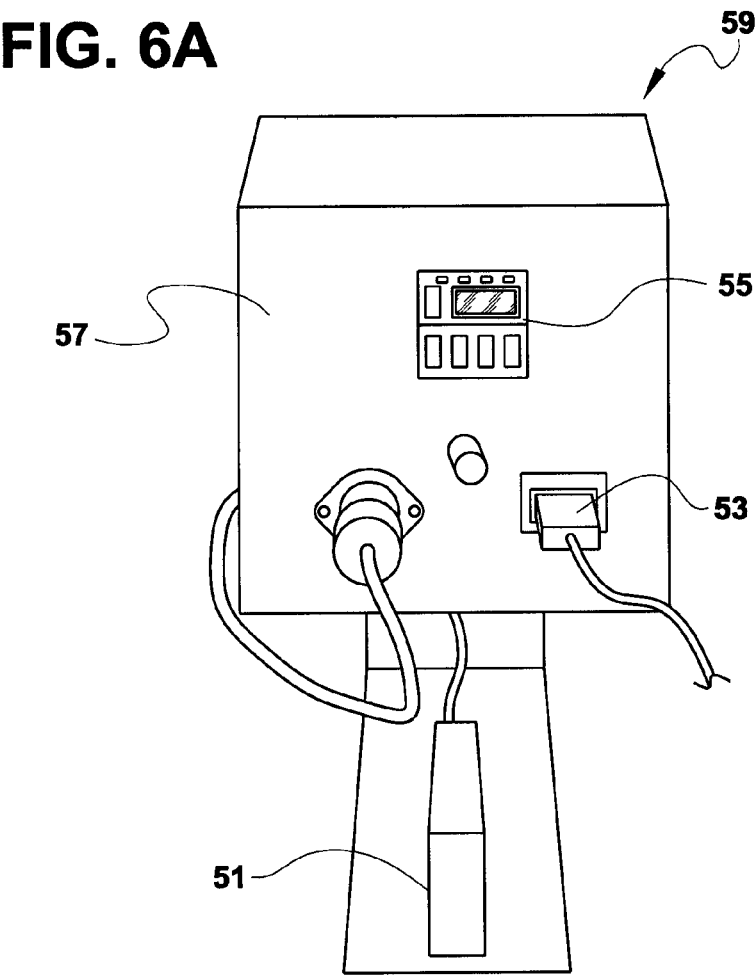
FIG. 6C
FIG. 6B
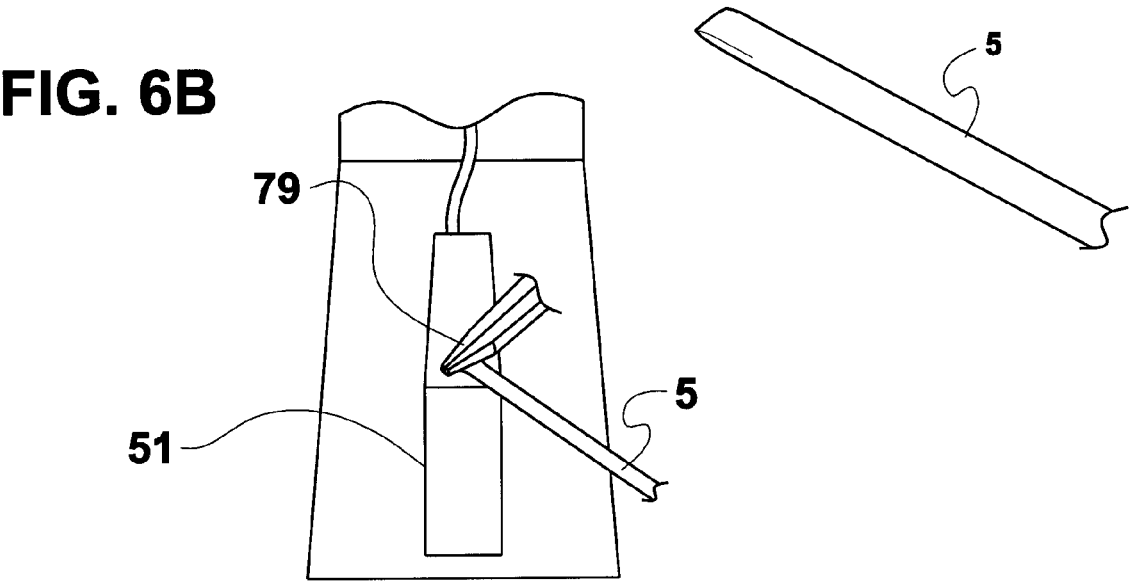

MULTILUMEN CATHETERS AND METHOD OF MANUFACTURING

CROSS REFERENCE TO RELATED APPLICATIONS

This application claims priority to U.S. Patent Application Ser. No. 61/148,078, filed Jan. 29, 2009, which application is incorporated herein by reference. This application is also related to commonly owned U.S. patent application Ser. No. 12/648,169, filed concurrently herewith, which is incorporated herein by reference in its entirety.

TECHNICAL FIELD

The present invention relates to multilumen catheters and methods of manufacturing the same.

BACKGROUND OF THE INVENTION

Vascular access catheters can be used for hemodialysis, a medical procedure used to cleanse the blood of patients whose kidneys do not function properly, by simultaneously extracting and returning fluids to the patient's body. Dual or triple lumen hemodialysis catheters have two or three longitudinal lumens extending the length of the catheter. In dual lumen hemodialysis catheters, one lumen can be dedicated for withdrawal of blood to be cleansed, known as the arterial or aspiration lumen, and another lumen can be dedicated for return of the cleansed blood to the central circulatory system. This lumen is also known as the venous or return lumen. The distal segment of the catheter is typically positioned at the junction of the superior vena cava and right atrium to obtain a blood flow of sufficient volume to accommodate dialysis treatment requirements. These and other types of multilumen catheters are typically constructed of two or more catheter tubes of the same shape, color, and a single thermoplastic material such as polyurethane. Such catheters can be extruded and then bonded together using chemicals, solvents, or adhesives to form a unitary catheter shaft for at least a portion of the overall catheter length. The chemicals, solvents, or adhesives can be placed along at least a partial or a complete length of the catheter tube surfaces in order to secure the tubes together. Outer sleeves can be used to hold multiple catheter tubes together around at least a portion of an exterior surface of multiple catheter tubes, such that at least a portion of the catheter tubes are fixed within the outer sleeve. Extrusion is another method of forming multilumen catheters. Extrusion involves pushing a melted resin through a die and into a cooling bath. The die size must be changed for each size catheter produced.

Another known process for producing multilumen catheters involves the use of platens. In this process, two or more catheter tubes are joined together and placed inside of a metal mold or platen that has an embedded shape of the catheter tubes. Typically, the platen is made of aluminum or another heat-conducting metal. Once the catheter is placed within the platen mold, the platens are then put between two heated metal plates and heated. The platens are then cooled to confer the desired shape to the catheter shaft that was placed inside of the platen molds. In another aspect, catheters can be manufactured using butt welding techniques, where at least one tube can be attached to the distal end of the catheter tubes such that the added tubes form a passageway with the catheter tubes and are in fluid communication with the added tubes.

The above described methods of manufacturing such catheters have several disadvantages. Multilumen catheter extrusion processes can be time-consuming and more costly to produce compared to single lumen catheter extrusion processes. Outer sleeves can be disadvantageous because they can be costly and more time consuming due to additional manufacturing steps. They can also add additional bulk to the catheter and may require additional steps during manufacturing. Chemical slurries or solvents can adversely affect or alter the physical properties of catheter tube materials, and in some cases, can cause the catheter tubes to degrade. They can also be difficult for a user to work with and can leave a messy residue behind that can leak or spill over the edges of the catheter tube surfaces. Such chemicals or solvents can be time-consuming, toxic, and hazardous for a user to dispose of. Chemical solvents or bonds can come apart over the course of time if the chemicals break down. There can also be a chance that the chemical solvent cannot be applied evenly or consistently to the surface of a catheter tube. This can lead to selected portions of the catheter tubes being more securely bonded than other portions, which can lead to weakness, kinking, or separation of the catheter tubes, thereby compromising the integrity of the catheter tubes and the treatment of the patient.

While platens are useful for bonding multiple catheter tubes together and conferring desired shapes to catheter shafts, the use of platens can cause the finished catheter shaft to take on the characteristics of the platen surface finish, and can cause the outer shaft of the catheter to have an undesirable surface finish, which is disadvantageous when placing the catheter into a patient's body. While extrusion techniques can produce catheters with very good surface finishes, if the catheter surface is re-heated in a platen mold, this re-heating can destroy the exterior surface of the catheter. The use of platen molds can also increase the catheter manufacturing time because a different type of platen mold is required for each catheter size and length. Butt welding techniques can be disadvantageous because the catheter tubes can become separated from the added catheter tube portions. A vascular access catheter and method of manufacturing such catheter has not yet been proposed that solves all of the above-mentioned problems.

Provided herein is an improved multilumen catheter and method of manufacturing multilumen catheters. The improved method of manufacturing the multilumen catheters described herein allows at least two catheter tubes to be consistently, reliably joined together longitudinally using a heat-bonding process, without the negative effects of chemical or solvent bonding processes, extrusion or outer sleeve processes, or the use of platen molds described above. During this process, at least a portion of at least two catheter tubes are heated and permanently joined along at least a portion of opposing internal surfaces of the catheter tubes together through an orifice of a die, to form a unitary multilumen catheter shaft.

It is a purpose of this invention to provide a catheter manufacturing process wherein the temperature of the heat used to heat at least a portion of the catheter tubes or the location of the heat can be adjusted to alter the strength of the bond between the catheter tubes. In this aspect, a permanent bond can be created between at least a portion of at least two catheter tubes, and a splittable bond can be created between at least a portion of the at least two catheter tubes.

It is a further purpose to provide a method of manufacturing that can incorporate different materials, such as wires, electrodes, or radiopaque materials, between the catheter tubes as the tubes are heat-bonded together.

It is a further purpose to provide a method of manufacturing that can be used to produce a catheter having a smooth outer surface finish for at least a portion of the catheter shaft because only a portion of the catheter inner surface is heated, and the finished outer surface portion of the catheter is not subjected to heat.

It is a further purpose to provide a method of manufacturing that can be used to produce catheter shafts having tubes with different durometers, tensile strengths, flexibilities, radiopacity, colors, lengths, outer shapes or lumen configurations, such as dual lumen or triple lumen, split tip or non-split tip, or other different properties, including splittable or peelable catheter shafts.

It is a further purpose to provide a method of manufacturing multilumen catheters that is more cost effective, faster, and safer compared to known catheter bonding methods.

Various other aspects and embodiments of the present invention will become apparent to those skilled in the art as more detailed description is set forth below. Without limiting the scope of the invention, a brief summary of some of the claimed embodiments of the invention is set forth below. Additional details of the summarized embodiments of the invention and/or additional embodiments of the invention may be found in the Detailed Description.

SUMMARY

A method of making a multilumen catheter assembly is provided that involves providing a plurality of tubes, each tube having a first end, a second end, at least one lumen, and at least one surface, selectively heating at least a portion of one tube of the plurality of tubes, and contacting the selectively heated portion of the surface of the first tube with a second tube to form a multilumen catheter shaft that is joined together along at least a portion of the length of the catheter shaft.

A multilumen catheter assembly is also provided. The multilumen catheter assembly has a catheter shaft having a plurality of tubes. Each tube has a proximal end, a distal end, at least one lumen extending longitudinally through at least a portion of each tube, and at least one surface. At least a portion of the inner surface of the first tube is selectively fused with at least a portion of the inner surface of the second tube along at least a portion of the longitudinal length of the catheter shaft.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIGS. 4A through 4C illustrate partially broken away plan views of additional embodiments of the distal portion of the catheter shaft of FIG. 1 that can be produced by the manufacturing process described herein.

FIGS. 6A through 6C illustrate partial perspective views of a method of sealing the ends of the catheter shaft of FIG. 1 for the catheter manufacturing process described herein.

DETAILED DESCRIPTION

Figure 1:
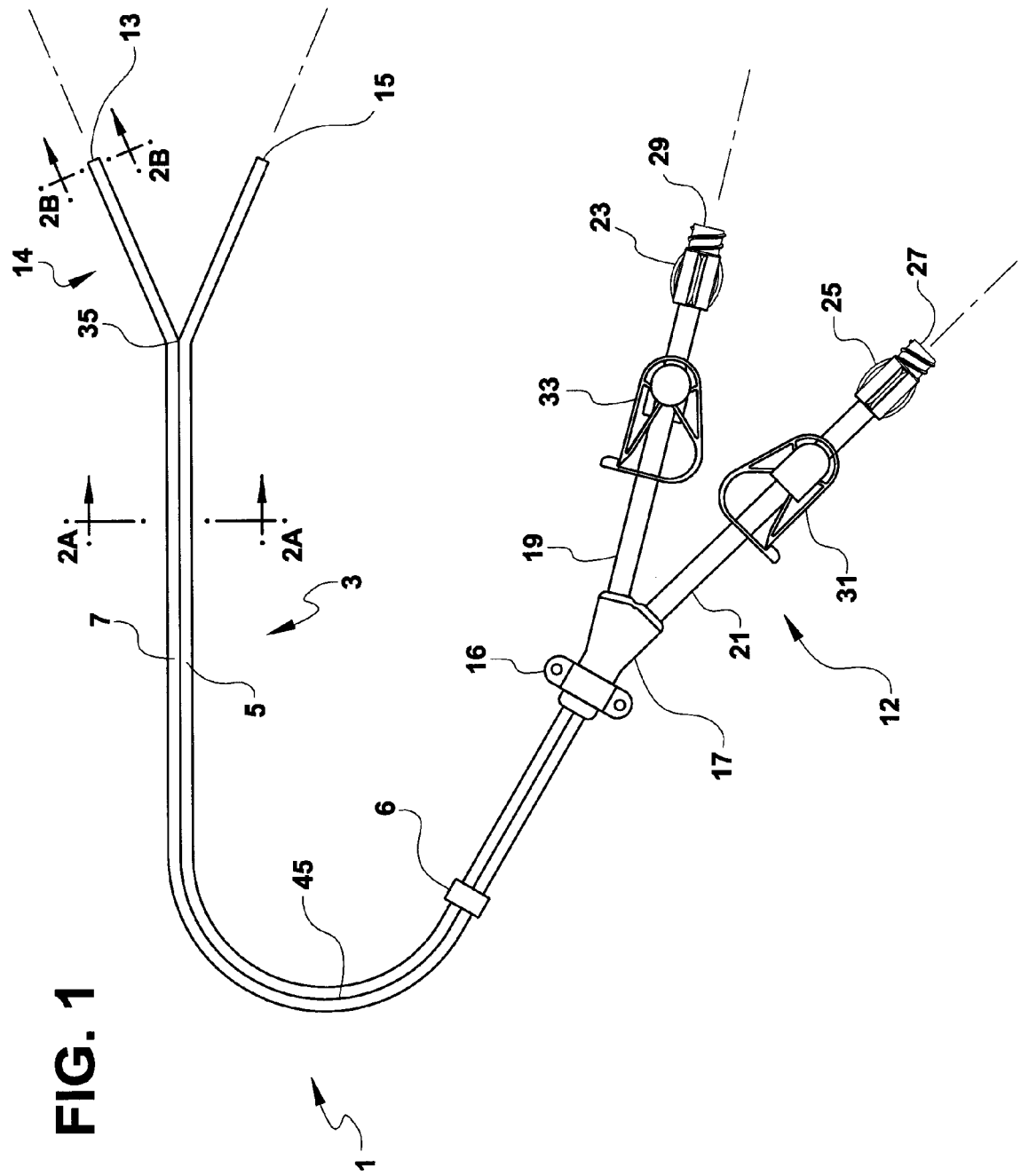
FIG. 1 illustrates a top plan view of one embodiment of a multilumen split-tip catheter, such as a hemodialysis catheter, that can be produced by the method of manufacturing multilumen catheters disclosed herein.

The present invention can be understood more readily by reference to the following detailed description and the examples included therein and to the Figures and their previous and following description. The drawings, which are not necessarily to scale, depict selected preferred embodiments and are not intended to limit the scope of the invention. The detailed description illustrates by way of example, not by way of limitation, the principles of the invention.

The skilled artisan will readily appreciate that the devices and methods described herein are merely exemplary and that variations can be made without departing from the spirit and scope of the invention. It is also to be understood that the terminology used herein is for the purpose of describing particular embodiments only and is not intended to be limiting. All dimensions provided herein are for illustrative purposes only, and actual dimensions may be higher or lower.

Ranges can be expressed herein as from "about" to one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. As used herein, the words "proximal" and "distal" refer to directions away from and closer to, respectively, the insertion tip of the catheter in the catheter assembly. The terminology includes the words above specifically mentioned, derivatives thereof, and words of similar import.

"Optional" or "optionally" means that the subsequently described element, event or circumstance can or cannot occur, and that the description includes instances where said element, event or circumstance occurs and instances where it does not. Referring now in detail to the drawings, in which like reference numerals indicate like parts or elements throughout the several views, in various embodiments, presented herein is an exemplary multilumen catheter, such as a dialysis catheter, and a method of manufacture of said multilumen catheter.

FIG. 1 illustrates one exemplary embodiment of a multilumen vascular access catheter, such as a hemodialysis catheter, that can be produced by the method of manufacturing described herein. The catheter assembly 1 has a proximal end 12 and a distal end 14. In one aspect, the catheter can be comprised of a unitary catheter shaft 3. In one aspect, the catheter shaft 3 of the catheter assembly 1 can be comprised of any suitable biocompatible plastic or elastomeric material, such as, but not limited to polyurethane and polyethylene, or soft silicone elastomers. In one aspect, the catheter shaft can be composed of a Carbothane® material. In yet another exemplary aspect, the catheter shaft can be composed of Carbothane® PC3585A-B20. In one aspect, the catheter shaft can be pre-curved, as illustrated in FIG. 1, or it can be straight. In one aspect, a bifurcate or hub 17 surrounds at least a portion of the outer surface of proximal portion 12 of the catheter shaft 3. In one exemplary aspect, the bifurcate 17 can be composed of Carbothane® PC3585A-B20. In one aspect, the catheter shaft 3 can be comprised of at least a first tube 5 and a second tube 7. In one aspect, the tubes 5, 7 can extend substantially the entire length of the catheter assembly 1. In one aspect, tube 5 has an outer surface 47 and tube 7 has an outer surface 43 (shown in FIGS. 2A-2D). In one aspect, as illustrated in FIG. 2C, tube 5 can have an outer surface 47 and an inner surface 81, and tube 7 can have an outer surface 43 and an inner surface 79. In one aspect, as illustrated in FIG. 2A, the inner surfaces 79, 81 can be substantially flat or planar.

Cuff 6, which facilitates anchoring for tunneled catheters, can optionally be attached to at least a portion of the surfaces 43, 47 of catheter tubes 5, 7 of the unitary catheter shaft 3. In one aspect, the cuff 6 can is useful for allowing subcutaneous tissue to grow into the cuff 6 and to help secure the catheter once it is implanted in a patient's body. In one exemplary aspect, the cuff 6 can be composed of polyester or Dacron. In one aspect, the catheter assembly 1 can have at least a first extension tube 19 and a second extension tube 21 and at least a first extension tube clamp 33 and a second extension tube clamp 31. In one aspect, the clamps 33, 31 can be releasably attached to each extension tube 19, 21. In one aspect, although not shown, optionally at least one of the catheter extension tubes 19, 21 can have at least one pre-curved portion. In one aspect, the at least one pre-curved portion can enable the extension legs to extend downward against a patient's body once the distal portion of the catheter assembly has been placed in a patient's vasculature. This design is beneficial because it can provide greater comfort for the patient. In one exemplary aspect, the extension tubes 19, 21 can be made of clear Carbothane® PC3595A. In another exemplary aspect, the clamps 31, 33 can be composed of Acetal/Tecoflex. In one aspect, the catheter assembly 1 has at least a first catheter hub connector or luer connector 23 and a second catheter hub connector or luer connector 25 for joining to a dialysis machine or other injection or aspiration device in order to provide intravascular access to the patient. In one exemplary aspect, the luer connectors 23, 25 can be composed of Isoplast 2510. In another aspect, the catheter shaft 3 can have a suture wing 16 for providing securement of the catheter body to the patient. In one exemplary aspect, the suture wing 16 can be composed of Pellathane®.

Figure 2A:
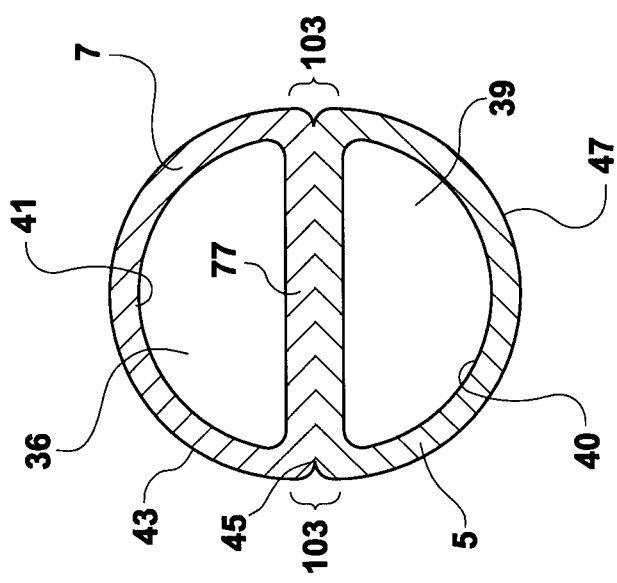
FIGS. 2A and 2B illustrate cross-sectional views of the catheter shaft of the catheter of FIG. 1 taken along lines 2A-2A, and 2B-2B.

When the catheter assembly 1 is connected to a dialysis machine (not shown), blood is withdrawn from a patient's venous system and transported through second lumen or arterial lumen 39, illustrated in FIG. 2A, of withdrawal or aspiration tube 5 at opening 15 for cleansing by the dialysis machine. In one aspect, the second or arterial lumen 39 extends from the proximal end to the distal end portion of the catheter shaft 3. Aspiration of the blood through aperture 15 of tube 5 is accomplished by drawing a vacuum or negative pressure, causing the blood to be drawn through the catheter into the dialysis machine. The treated blood is then returned to the central venous system through opening 27 of luer connector 25 which is connected to the dialysis machine, into infusion or venous tube 7 with first lumen or venous lumen 36 (FIG. 2A), under pressure, through distal opening 13 into the patient's bloodstream. In one aspect, the first or venous lumen 36 extends from a proximal end to a distal end of the catheter shaft. In one aspect, first and second extension tubes 19, 21 are fluidly joined with or in fluid communication with lumens 39, 36, respectively so as to enable the infusion or aspiration of fluids from the central venous system of a patient. In one aspect, lumens 36, 39 can extend generally longitudinally parallel to each other along a longitudinal axis, such that lumen 36 is positioned on one side of the longitudinal axis, and lumen 39 is positioned on a second side of the longitudinal axis. Although primarily used for dialysis, the multilumen catheter described herein can also be used for other exemplary processes, such as, but not limited to, plasmapheresis, perfusion, infusion, and chemotherapy.

As illustrated in FIG. 1, at least a portion of the catheter tubes 5, 7 are bonded or fused together to form a unitary catheter tube. More particularly, at least a portion of the catheter tubes 5 and 7 can be joined together along at least a portion of inner surfaces 79, 81, illustrated in FIGS. 2A and 2C, such that the combined surfaces form a unitary septum 77, illustrated in FIGS. 2A and 2D. In one exemplary embodiment, the septum 77 can have a thickness of between about 0.020 inches to about 0.050 inches. More particularly, the septum 77 can have a thickness of between about 0.024 inches to about 0.036 inches.

In one aspect, although the manufacturing method described herein can produce a catheter shaft 3 having a split tip distal tip catheter configuration, the catheter shaft 3 can also have various types of distal tip configurations, such as, but not limited to dual lumen or any multilumen configuration, split tip (FIGS. 1, 4C, 5A), staggered or stepped tip (FIG. 4A), or other types of split tip and non-split tip distal tip catheter configurations. In one exemplary aspect, to produce the catheter described in any of FIGS. 1 through 5C, at least two catheter tubes having D-shaped lumens, as described above, can be used in this process.

Figure 2B:
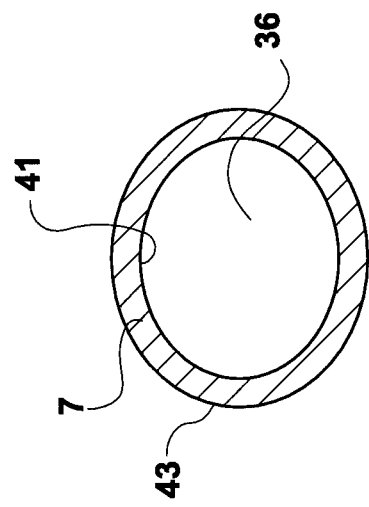
Figure 2C:
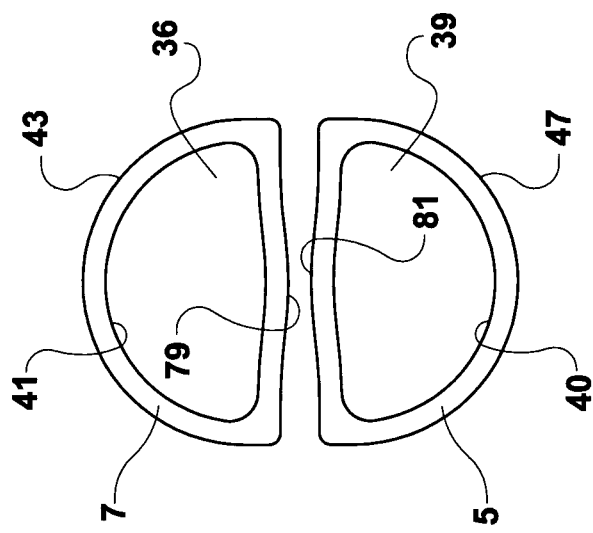
FIG. 2C illustrates an end view of an additional embodiment of the catheter tubes before they are joined using the manufacturing method disclosed herein.

In one aspect, at least a portion of each of catheter tubes 5, 7 can be bonded together to form a unitary catheter shaft 3 using a heat bonding or fusing process as described herein. This process forms a heat fusion bond between at least a portion of a surface of catheter tube 5 and a portion of a surface of catheter tube 7 from the hub 17 to a dividing point 35 for at least a portion of the overall catheter length. In one aspect, catheter tubes 5, 7 can be of the same length, such as illustrated in FIGS. 1 and 4B. In one aspect, the catheter tubes can be fused along an entire length of the catheter shaft, as illustrated in FIG. 4B. In another aspect, the method of manufacturing described herein can produce catheters having catheter tubes 5, 7 can be of different lengths, such as illustrated in FIGS. 4A and 4C. As illustrated in FIGS. 2A and 2B, several cross sectional views of the distal portion 14 of the catheter assembly of FIG. 1 are shown. Although shown in a round or circular cross-sectional shape along line 2A-2A, catheter tubes 5, 7 can be of other cross-sectional profiles including D-shaped, oval, elliptical, or any other suitable lumen configuration, diameter, material, thickness, or length, in any combination thereof. As shown along the cross-section 2A-2A of FIG. 1, arterial tube 5 has an arterial lumen 39 with an inner lumen surface 40 and an outer surface 47. In one aspect the portion of the catheter tube 5 that is defined between the outer surface 47 and the inner lumen surface 40 defines the tube sidewall. In one aspect, venous tube 7 has a venous lumen 36 with an inner lumen surface 41 and an outer surface 43. The catheter tubes 5, 7 used herein can each have a diameter or width of the inner surfaces 79, 81 of approximately 0.175 inches and a height of approximately 0.105 inches. Each lumen 36, 39 can have a width of approximately 0.106 inches at their widest point and a height of approximately 0.073 inches.

In one aspect the portion of the catheter tube 7 that is defined between the outer surface 43 and the inner lumen surface 41 defines the tube sidewall. Each catheter tube can have a substantially equal wall thickness. Alternatively, each catheter tube 5, 7 can have a varying wall thickness. For example, the wall thickness can vary from about 0.010 inches to about 0.050 inches. More particularly, the wall thickness of each catheter tube can vary from about 0.012 inches to about 0.040 inches. In one embodiment, the outer diameter of the catheter shaft 3 can be about 0.207 inches. In one aspect, catheter tubes 5, 7 are preferably designed to maximize the cross-sectional diameter of the lumens 36, 39 to achieve increased flow rates during dialysis. As illustrated in FIG. 2A, in one aspect, the cross-sectional area of the D-shaped lumens 36, 39 can be substantially equal. In yet another aspect, the cross-sectional area of the D-shaped lumens 36, 39 can have different cross-sectional areas. For example, lumen 36 can have a first cross-sectional area, and lumen 39 can have a second cross-sectional area. In one aspect, lumen 36 can have a longitudinal length and a larger cross-sectional area than lumen 39 along at least a portion of its longitudinal length. Alternatively, in another aspect, lumen 39 can have longitudinal length and a larger cross-sectional area than lumen 36. In one aspect, the venous and arterial lumens 36, 39 are configured so as to accommodate fluid flow rates required for hemodialysis, i.e., about 300 ml/min. at about 250 mm Hg pressure.

In one aspect, a slight indentation or "v-shape" 103 can be defined in the outer surface of the catheter shaft 3 as a result of the manufacturing process described herein. This "v-shape" can be defined at opposing outer edges of the catheter tubes 5, 7, as illustrated in FIG. 2A, when at least a portion of the catheter tubes 5, 7 have been joined together using the heat-bonding manufacturing process described herein. The v-shaped indentation 103 can be varied such that it is clearly visible to an observer. In another exemplary embodiment, the v-shape can be visible only using microscopic guidance. In one aspect, this slight v-shaped indentation 103 can serve to assist the user or manufacturer in identifying the location and type of the at least two catheter tubes 5, 7 relative to each other. In yet another exemplary embodiment, as illustrated in FIG. 5C, the outer surface of the catheter shaft 3 can be uniformly smooth across substantially the entire outer surface of the catheter shaft 3 such that no v-shape indentation is visible in the outer surface of the catheter shaft 3 either to an ordinary observer or under microscopic guidance.

FIG. 2C depicts one exemplary embodiment of catheter tubes 5, 7 before they are heat bonded together. In this aspect, the arterial and venous lumens 39, 36 are substantially D-shaped and are dimensioned to optimize performance of each of the catheter tubes 5, 7. In one exemplary aspect, at least a portion of the inner surfaces 79, 81 can be contoured, as illustrated. In one aspect, as illustrated in FIG. 2C, at least a portion of inner surface 79 of tube 7 can be slightly bowed outward away from the D-shaped lumen of tube 7, and at least a portion of the surface 81 of tube 5 can be slightly bowed outward away from the D-shaped lumen of tube 5. In one aspect, at least a portion of the convex inner surfaces 79, 81 can be dimensioned to ensure that at least a portion of each of the center portions of each of the inner surfaces 79, 81 are in contact with each other and with a heating means, described herein, during the manufacturing process.

As illustrated in FIGS. 2A and 2C, in one exemplary aspect, at least a portion of the inner surfaces 79, 81 can face each other such that at least a portion of the inner catheter surfaces 79, 81 are internally opposed to each other before and after they are joined together. In the assembled multilumen catheter that is produced by the process described herein, at least a portion of a first catheter tube 5 can be joined to at least a portion of a second catheter tube 7. More particularly, in one exemplary aspect, at least a portion of the surface of the first catheter tube 5 can be joined to at least a portion of the surface of the second catheter tube 7. In one aspect, at least a portion of inner surface 79 of venous tube 7 can be joined to at least a portion of inner surface 81 of arterial tube 5 such that at least a portion of the individual catheter tubes 5, 7 become bonded or fused to one another, along a joining line or interface 45, illustrated in FIG. 2A, to form a catheter shaft 3 having a unitary continuous smooth exterior or outer surface.

Figure 3A:
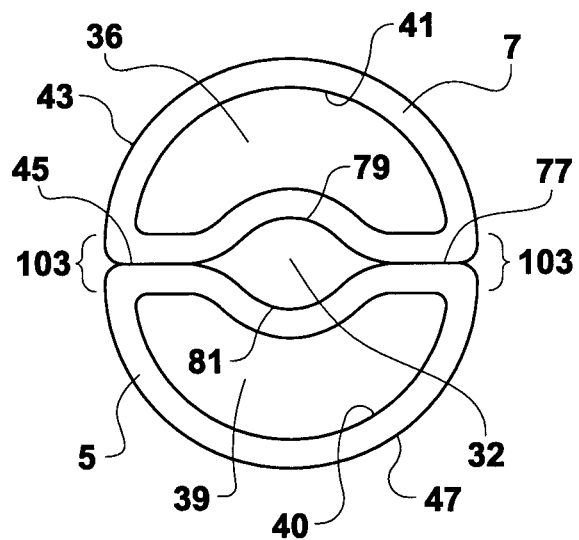
FIGS. 3A through 3D illustrate several exemplary cross-sectional views of different embodiments of the catheter shaft of FIG. 1 that can be produced by the manufacturing process described herein.
Figure 3B:
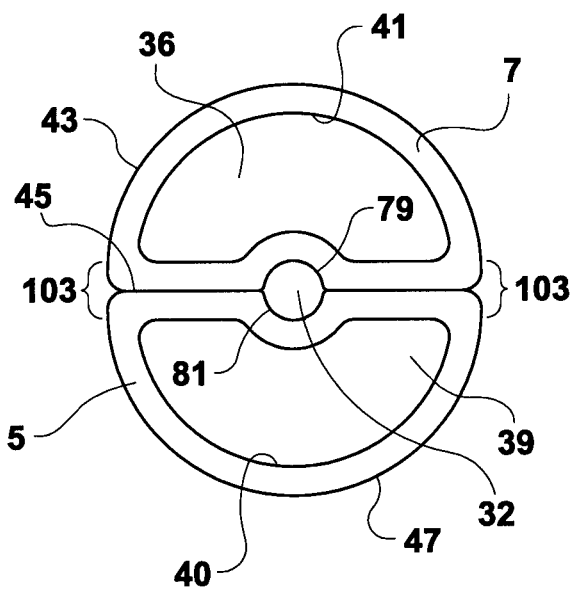

FIGS. 3A and 3B illustrate an additional embodiment of a catheter assembly that can be produced using the manufacturing process described herein. In one aspect, the catheter manufacturing method described herein can be used to produce a multilumen catheter shaft having more than two lumens. For example, a catheter having a third lumen 32 can be produced by the catheter manufacturing process described herein. In one aspect the additional third lumen 32 can be capable of selectively receiving at least a portion of a guide wire. The third lumen 32 can also be configured for the administration and withdrawal of fluids such as drugs or blood sampling, and for injection of contrast media through the third lumen 32 that is required for imaging procedures. In one exemplary aspect, as illustrated in FIGS. 3A and 3B, the third lumen 32 can be positioned between venous and arterial lumens 36 and 39. In one aspect, as illustrated, the third lumen 32 can be smaller in cross-sectional area than the first and second lumens 36, 39. In one aspect, as illustrated in FIG. 3A, the cross-sectional areas of the lumens 36, 39 can be substantially equal. The third lumen can have an aperture that can be positioned proximally of the distal apertures 13, 15 along the length of the catheter shaft. Each of the lumens 36, 39, and 32 can have at least one proximal aperture and at least one distal aperture, and at least portion of each aperture is in fluid communication with at least a portion of a respective lumen of the catheter shaft 3.

In one aspect, third lumen 32 can be centrally located within the interior of the catheter shaft 3. In one aspect, the third lumen 32 can be formed such that it has an inner surface comprising at least a portion of inner surfaces 79, 81 of catheter tubes 5, 7. In one aspect, the inner wall of the lumen 32 forms an annular inner surface 79, 81 that is configured to facilitate fluid flow within lumen 32. In another aspect, the third lumen 32 has an outer surface that is comprised of at least a portion of the inner lumen surfaces 41, 40 of lumens 36, 39. In this aspect, the outer surface of the third lumen 32 can form at least one arcuate surface.

In yet another exemplary aspect, lumen 32 can be positioned between lumens 9, 11 such that it is not positioned exactly in the center of the septum 77 in the interior of the catheter shaft 3. In one aspect, although not illustrated, the third lumen 32 can be positioned between lumens 36, 39 such that third lumen 32 is positioned at a point that is off-center within the septum 77 from the longitudinal axis of the catheter shaft 3. More particularly, in one aspect, the third lumen 32 can be positioned such that it is tangential to the longitudinal axis. In one aspect, the third lumen 32 can be configured for fluid flow in various directions. In one aspect, lumen 32 can be used simultaneously at the same time that lumens 36, 39 are being used. In one aspect, the third lumen 32 is not in fluid communication with lumens 9, 11. In one aspect, although lumen 32 can be used for the infusion of additional medications or fluids, lumen 32 can also be used for arterial and/or venous flow. Although primarily used for hemodialysis, the multilumen catheter described herein can also be used for other exemplary processes, such as, but not limited to, plasmapheresis, perfusion, infusion, and chemotherapy.

Extension tube 50 is fluidly joined with lumen 32 at the proximal portion 12 of the catheter assembly 1, so as to enable the infusion or aspiration of fluids from or to the central venous system of a patient. In one example, the third lumen 32 can have a generally smaller transverse cross-sectional area than the transverse cross-sectional area of lumens 39 and 36. The smaller cross-sectional area of the third lumen 32, compared to lumens 36, 39 is beneficial because it makes it easier to keep the third lumen 32 free of blood due to its smaller cross-sectional size. In yet another aspect, the position of the third lumen proximal of the distal tip portions can help to increase flow diversion so fluid is flowing out of the third lumen, and not just through the first and second lumens, which can help prevent catheter "tip whip". This is in contrast to prior art catheters in which a whipping action can occur due to the pressure of fluid exiting the return lumen, excessive movement of the catheter tip within the vessel, or by turbulent flow in the vessel near the tip of the catheter.

In this aspect, the third lumen 32 is configured or proportioned for slidably receiving at least a portion of a guide wire during insertion of the catheter assembly 1. The small size of the third catheter lumen also makes it easier to use a guide wire to replace a catheter which has clotted blood in the blood lumens without dislodging any blood clots which may have accumulated in the blood lumens. The lumen 32 can provide a guide wire track for a guide wire to facilitate insertion of the catheter assembly 1 through tissue into the target vessel and allows for improved guide wire insertion and tracking techniques. In one exemplary aspect, and not meant to be limiting, the inner diameter of third lumen 32 can be approximately between about 0.035 to about 0.038 inches to accommodate a guide wire. In one aspect, the inner diameter of the third lumen 32 can be approximately 0.037 inches so as to accommodate a guide wire with an outer diameter of approximately 0.035 inches, such that it is positioned in close surrounding relationship to at least a portion of an inserted guide wire. It is contemplated that other dimensions may be used for the third lumen 32 and the guide wire, provided such dimensions provide a close surrounding relationship between the third lumen 32 and at least a portion of guide wire. These dimensions allow the guide wire to be slidably and selectively received within the lumen 32, while minimizing space between the outer diameter of the guide wire and the inner diameter of the lumen 32. In another aspect, the third lumen 32 can also be configured to slidably receive other devices, such as, but not limited to filter retrieval or snare devices, a stylus or stylet, obturator, and the like. In one exemplary aspect, between uses, the third lumen 32 may be occupied by an obturator or other blocking device, if desired.

Figure 3C:
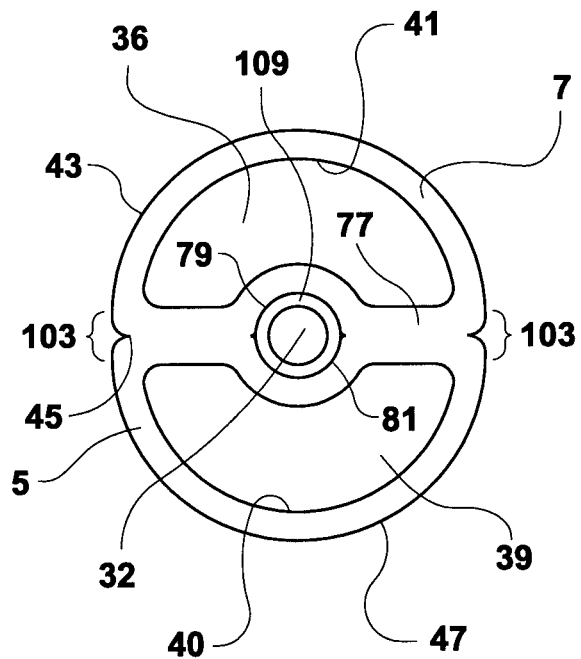

In the triple lumen configurations illustrated in FIGS. 3A through 3C, at least a portion of the catheter tubes 5, 7 can be joined together along at least a portion of inner surfaces 79, 81 such that the combined surfaces form an integral, internal, bisecting planar septum 77. The septum 77 can extend diametrically across the interior of the catheter shaft 3 and defines lumens 36, 39, 32, such that both lumens 36, 39 are substantially C-shaped in transverse cross-section, and third lumen 32 is substantially circular in transverse cross-section. In one aspect, lumen 32 bisects septum 77 along a length of the catheter shaft 3.

In one exemplary embodiment, as illustrated in FIG. 3C, a liner or tube 109 can be positioned thereon at least a portion of the inner wall 79, 81 of the third lumen 32. In this aspect, the liner or tube can provide additional strength and can function as a lubricious coating to the third lumen 32. In one aspect, the liner 109 can be comprised of nylon or any other suitable material. In one aspect, the liner or tube 109 can be used for high pressure injections, as described above.

In addition to allowing blood draws and fluid aspiration/infusion therethrough, in one aspect, the third extension tube 50 can be used as a power injection tube to enable rapid infusion of contrast media into lumen 32, such as that used during contrast-enhanced CT scan imaging. In another aspect, the third lumen 32 can be used to infuse other fluids into the patient. In one aspect, fluids can be infused into the extension tube 50 and lumen 32 at a rate of between about 2 milliliters per second and about 10 milliliters per second and at a fluid pressure of between about 50 psi and about 300 psi, although one of ordinary skill will recognize that other flow rates and fluid pressures are also possible. In one aspect, the extension tube 50 and the third lumen 32 can also be used to remove blood or other fluids alone or during simultaneous use of the first and second lumens.

In an alternative embodiment, the liner 109 can be positioned on at least a portion of the inner wall 79, 81 of the lumen 32 to form a reinforced lumen 32 that is configured to selectively receive at least a portion of a guide wire or other device and can be in surrounding relationship to a guide wire that can be inserted into the lumen 32, as described above. In this aspect, the liner 109 can be a tubular structure that functions to increase the burst pressure of the guide wire lumen 32. Burst pressure is defined herein as the amount of pressure that the lumen 32 may withstand during high pressure applications, such as contrast media injections, before rupturing. In this aspect, the liner 109 can be formed of a liner material with a higher yield stress than the material of the catheter shaft 3.

In various aspects, the liner 109 can protect the inner wall 79, 81 of the lumen 32 from erosion due to drug and chemical use, thereby allowing the catheter assembly 1 to be more resistant to drug therapy, and also supports high pressures for the purpose of CT injection, thereby allowing the catheter to be effectively used for high pressure CT injection, and eliminating the need for the placement of vascular access ports. As noted above, the liner 109 may be made of any suitable material that may increase the burst pressure of the lumen 32, such as, but not limited to, nylon, polyamide, and the like. The liner 109 can also function to reduce friction over the guide wire, which enhances the guide wire tracking capabilities of the lumen 32. In one example, the liner 109 may have a wall thickness of between approximately 0.002 and 0.005 inches. Optionally, the liner 109 can comprise a higher strength material than the catheter shaft 3 to allow for the formation of thinner surrounding catheter wall sections, thereby minimizing reduction in luminal cross-sectional area of the lumens 36, 39.

Figure 3D:
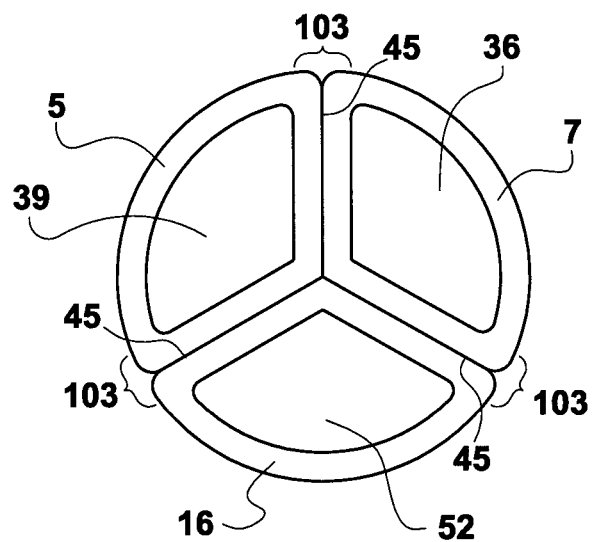

In one exemplary aspect, a cross-sectional configuration of an alternative triple lumen catheter assembly is illustrated in FIG. 3D. In one aspect, at least a portion of three catheter tubes 5, 7, and 16 can be joined together along at least a portion of their respective surfaces or to form a single catheter shaft of equally dimensioned catheter lumens using the catheter method of manufacturing disclosed herein. In one aspect, lumens 36, 39, and 52 can be of different sizes.

In yet another aspect, the catheter described herein can also have a quadruple lumen configuration (not illustrated). In this aspect, the catheter shaft can have four catheter tubes that are joined together along at least a portion of their respective surfaces or to form at least a first lumen, a second lumen, a third lumen, and a fourth lumen. In one aspect, in any of the embodiments described herein, the catheter assembly can be produced using catheter tubes having different materials, colors, durometers, or other characteristics. These characteristics can include, but are not limited to, tensile strength, durometer, rigidity or flexibility, radiopacity, cross-sectional luminal area, torquability, trackability, pushability, surface finish, and color. This can be done using different heat block configurations, such as, but not limited to, for example, star-shaped patterns, pie-shaped patterns with different sized pie shapes, or other various configurations.

Figure 5A:
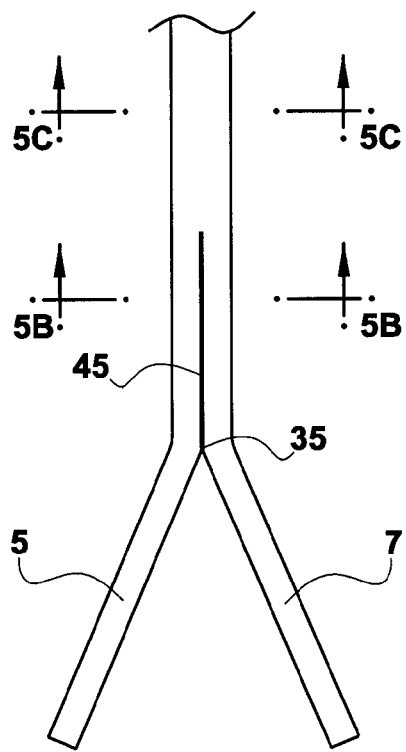
FIG. 5A illustrates a partially broken away plan view of a distal portion of an additional embodiment of the catheter shaft of FIG. 1 that can be produced using the catheter manufacturing method disclosed herein.
Figure 5B:
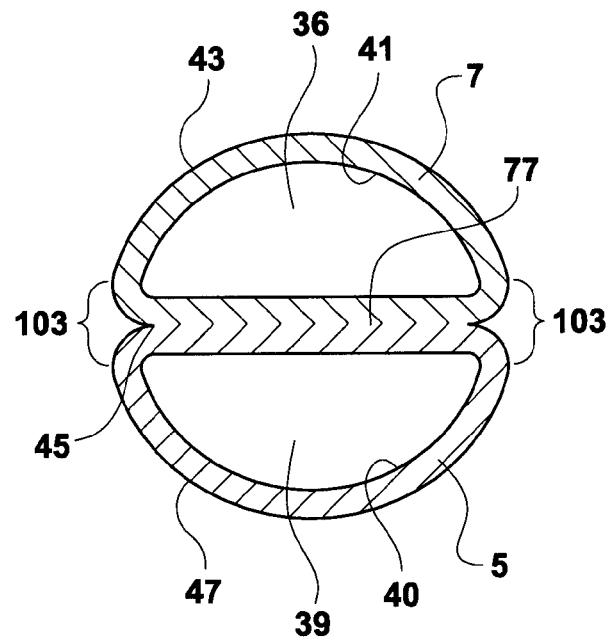
FIG. 5B illustrates a cross-sectional view of the catheter shaft of FIG. 5A along line 5B-5B.
Figure 5C:
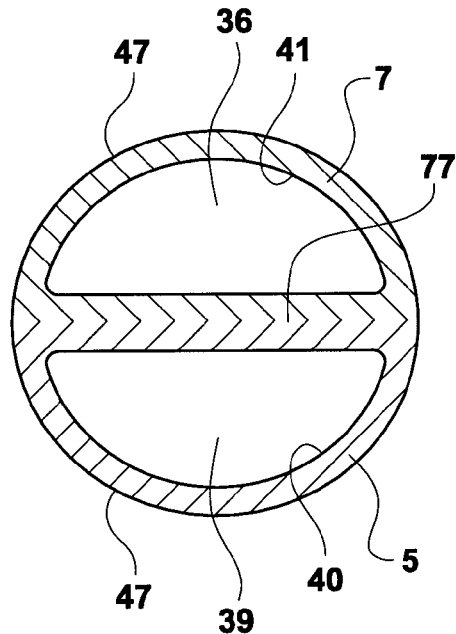
FIG. 5C illustrates a cross-sectional view of the catheter shaft of FIG. 5A along line 5C-5C.

FIGS. 5A through 5C illustrate yet another embodiment of the catheter shaft configuration that is produced by the catheter manufacturing method described herein. In one aspect, as illustrated in FIG. 5A, a heat fusion bond can be formed at an interface 45 of at least a portion of the surface of tube 5 and a portion of the surface of tube 7. In one aspect, at least a portion of the catheter tubes 5, 7 can be split distally of dividing point 35 such that at least a portion of the distal portion 14 of the catheter tubes 5, 7 are capable of independent (i.e., separate and free) movement relative to one another and are not attached to each other distally of dividing point 35. Alternatively, the catheter tubes 5, 7 can be shaped by heat to have a specific shape or configuration. In one aspect, during the manufacturing process described herein, at least a portion of the surface of each of the catheter tubes 5, 7 can be joined by a heat fusion bond for at least a partial length such that the tubes 5, 7 can be splittable or releasably attached, so that at least a portion of the distal portion of the catheter tubes are capable of independent movement relative to one another. Splittable or releasably attached means that at least a portion of the distal ends of the catheter tubes 5, 7 of catheter shaft 3 are capable of becoming separated or unattached from the distal ends to a pre-determined dividing point 35 upon applying minimal force to at least a portion of the catheter tubes 5, 7. In one aspect, approximately one to five pounds of force can be sufficient to separate at least a portion of the catheter tubes 5, 7. In one aspect, the distal ends can be defined in the same plane as distal openings 13, 15. In one aspect, at least a portion of the catheter tubes 5, 7 can be split apart along at least a portion of the catheter tubes 5, 7. After the tubes 5, 7 are pulled apart, the tubes 5, 7 become free-floating relative to each other. In one aspect, at least a portion of the catheter tubes 5, 7 can be split longitudinally apart along a longitudinal axis by holding at least a portion of each tube 5, 7 and manually pulling each tube in an opposite direction from each other.

In one alternative embodiment, instead of heat-bonding the entire inner surfaces 79, 81 of the catheter tubes 5, 7 using the catheter manufacturing process described herein, in one aspect the surfaces 79, 81 of the catheter tubes 5, 7 can be heated-bonded along at least a portion of the surfaces 79, 81 of the catheter tubes 5, 7 such that they form a segmented or alternating heat bond that can be separated to allow at least a portion of the catheter tubes 5, 7 to remain independent of one another. In one aspect, the heat-bonding process can be varied such that the density and size of the alternating heat bond can be altered to allow for different bonding strengths between the at least two catheter tubes 5, 7. In one exemplary aspect, the heat-bonding process described herein can be used to create an alternating heat bond between the catheter tubes 5, 7 that is of a pre-determined length and width. In one aspect, the alternating heat bond can be created and/or altered by simultaneously covering certain portions of the catheter tube surfaces that are being joined together to create at least one desired heat-bonding zone. This design can produce a splittable catheter shaft, as illustrated in FIG. 5A.

The alternating heat fusion bonds described herein allow the catheter tubes 5, 7 to be split apart evenly, such that at least a portion of the septum 77 can become divided, and the substantially equally dimensioned tube sidewall thickness of each tube 5, 7 is not compromised. In one aspect, an alternating pattern of heated and non-heated contact points between a portion of the surfaces of each of tubes 5, 7 can be created during the manufacturing process described herein. In one aspect, the alternating pattern can comprise any desired shape or configuration of heated and non-heated contact points between tubes 5, 7. The heat fusion bond portions can vary in distance from one another, in size, and in number. This alternating configuration can allow at least a portion of the catheter tubes 5, 7 to be split apart. In one aspect, the alternating bond length can be varied. The splittable catheter configuration described herein can be advantageous because it allows a practitioner to trim the distal ends of the tubes 5, 7 to a desired length, which can be desirable when treating patients of different sizes. This can enable a practitioner to manually adjust the length of the split tip portion of the catheter after the catheter is implanted in a patient. In one aspect, as illustrated in FIG. 4C, the splittable heat fusion bond can be used with a catheter having various lengths of catheter tubes 5, 7.

In yet another embodiment, at least one electrical wire or a shape memory wire can be embedded within at least a portion of the sidewalls of catheter tubes 5, 7. In one aspect, if more than two catheter tubes are used, the at least one wire can be embedded between more than one of the inner surfaces 79, 81 of the catheter tubes. In one aspect, the at least one wire can be formed of a material such as nitinol, stainless steel, nickel, titanium or alloys of nickel, or other types of suitable metal. In one aspect, if a nitinol wire is used, the wire can allow a user to twist or bend the finished unitary catheter shaft such that it has a desired bend or shape after the wire has been embedded between the catheter tube layers. In one aspect the wire can be embedded in various positions within the unitary catheter. The at least one embedded wire can be used to enhance the pushability, visibility, and strength of the catheter. In one aspect, the at least one wire can be radiopaque.

In one aspect, as described in U.S. application Ser. No. 11/074,504, and incorporated herein by reference, the catheter shaft 3 can include a plurality of wires that are electrodes that can be embedded anywhere within the catheter shaft. In one aspect, the electrodes can vary in size, shape, and length, can be positive or negative, and can be embedded in at least a part of the catheter shaft. In one aspect, the at least one wire can be round. In another aspect, the at least one wire can have a different shape, such as flat or curved. In one aspect, the at least one electrode can extend for at least a partial length within the catheter shaft and can function to connect each electrode to a source of electrical energy in the form of a generator (not shown). In one aspect, the at least one electrode can be comprised of any suitable electrically conductive material, including, but not limited to, stainless steel, gold, silver, nitinol, or other metals.

In one aspect, at least a portion of the inner surfaces 79, 81 of the catheter tubes 5, 7 can be combined with a radiopaque filler material to customize the physical characteristics of the venous and arterial tubes 5, 7. Radiopaque filler material can be used to enhance the visibility of the device under fluoroscopy. In one exemplary aspect, radiopaque material can be embedded onto or interspersed throughout at least a portion of the inner surfaces 79, 81 of the catheter tubes 5, 7 at a pre-determined distance to create equally spaced apart radiopaque markers. In one aspect, the radiopaque material or markers can comprise barium sulfate, zirconium dioxide, tantalum, tungsten, platinum, gold, silver, stainless steel, titanium, or any alloys thereof that are suitable for radiopacity. In one aspect, the radiopaque materials can also function as a reinforcing means of at least a portion of the tubes 5, 7.

In one aspect, the radiopaque material or markers can be embedded within at least a portion of the septum 77 that is formed by at least a portion of the surface of tube 5 and at least a portion of tube 7 that are joined together. Radiopaque material, which provides increased radiopacity, allows a practitioner to more accurately position the venous tip 13 of the catheter assembly 1 within the right atrium due to the increased visibility of the tip 13 under fluoroscopy. In one aspect, embedding radiopaque material between at least a portion of the inner surfaces 79, 81 of the catheter tubes 5, 7 can eliminate the need to put radiopaque marker bands around the outer surface of the catheter shaft.

The radiopaque markers can be beneficial because they can function as an internal marker band that is embedded within the catheter shaft and does not interfere with the insertion of the catheter shaft or the interior of the catheter shaft. In one exemplary aspect, if the catheter is being coated on the exterior surface, then the radiopaque markers will not interfere with the coating(s). This design is also beneficial because it allows fewer foreign materials to be exposed to the patient's body and fewer external bands around the catheter shaft, which bands could otherwise become dislodged or loose inside the patient. In one aspect, radiopaque material can be pre-embedded within a sidewall of at least one of the catheter tube. Alternatively, radiopaque material can be inserted between at least a portion of the catheter tube 5, 7 surfaces through a receiving means, described herein, that can be positioned between the two catheter tubes 5, 7 surfaces during the heat-bonding manufacturing process described herein.

In one aspect the manufacturing process described herein can be used to produce any type of multilumen catheter, such as, but not limited to, dialysis catheters, peripherally inserted central catheters (PICCs), angiographic catheters, balloon angioplasty catheters, or other types of catheters. In one aspect, the catheter shaft configuration and method of manufacturing described herein can be used with other types of catheter configurations. In one aspect, during the manufacturing process described herein, no chemical or solvent compositions are applied to any portion of the catheter tube surfaces to bond the surfaces of the catheter tubes.

The method of catheter manufacturing described herein involves several steps. Referring to FIGS. 6A through 6C, before the manufacturing process is begun, at least two catheter tubes 5, 7 are provided. In one aspect, each catheter tube 5, 7 has a first end and a second end. In one aspect, at least a portion of one end or a first end of at least one catheter tube is temporarily sealed. More particularly, at least a portion of a first end of at least one of the catheter tubes 5, 7 that are to be joined together can be temporarily sealed in order to allow the catheter tubes 5, 7 to remain pressurized during the catheter tube joining process. To complete this step of the process, a sealing means can be used. In one aspect, the sealing means can comprise a tubing closure assembly 59, as illustrated in FIG. 6A. In one aspect, the tubing closure assembly 59 can comprise a housing 57 that comprises a sealing temperature controller 55 and a thermocouple 53. The housing 57 is electrically connected to at least one sealing block 51. In one exemplary aspect, the sealing block 51 can be heated to approximately 250° F. by the sealing temperature controller 55 before at least one catheter tube 5, 7 is sealed. In another aspect, any suitable temperature can be used to seal at least one end of at least one of the catheter tubes 5, 7. In one aspect, at least a portion of a distal end of at least one of catheter shaft tubes 5, 7 can be sealed by placing at least a portion of the distal portion of at least one of the tubes 5, 7 on the sealing block 51 and applying pressure to the open ends of the tubes 5, 7 using an object such as a metal tool 79 to seal the tubing. As high temperature and high pressure is applied to at least a portion of the distal portion of at least one of the catheter tubes 5, 7, at least a portion of the open lumens of the catheter tubes 5, 7 can become sealed shut, as illustrated in FIG. 6C. The portion of the catheter tubes 5, 7 that has been heat sealed will be cut off and discarded at the finishing stage of the catheter manufacturing process.

Figure 10:
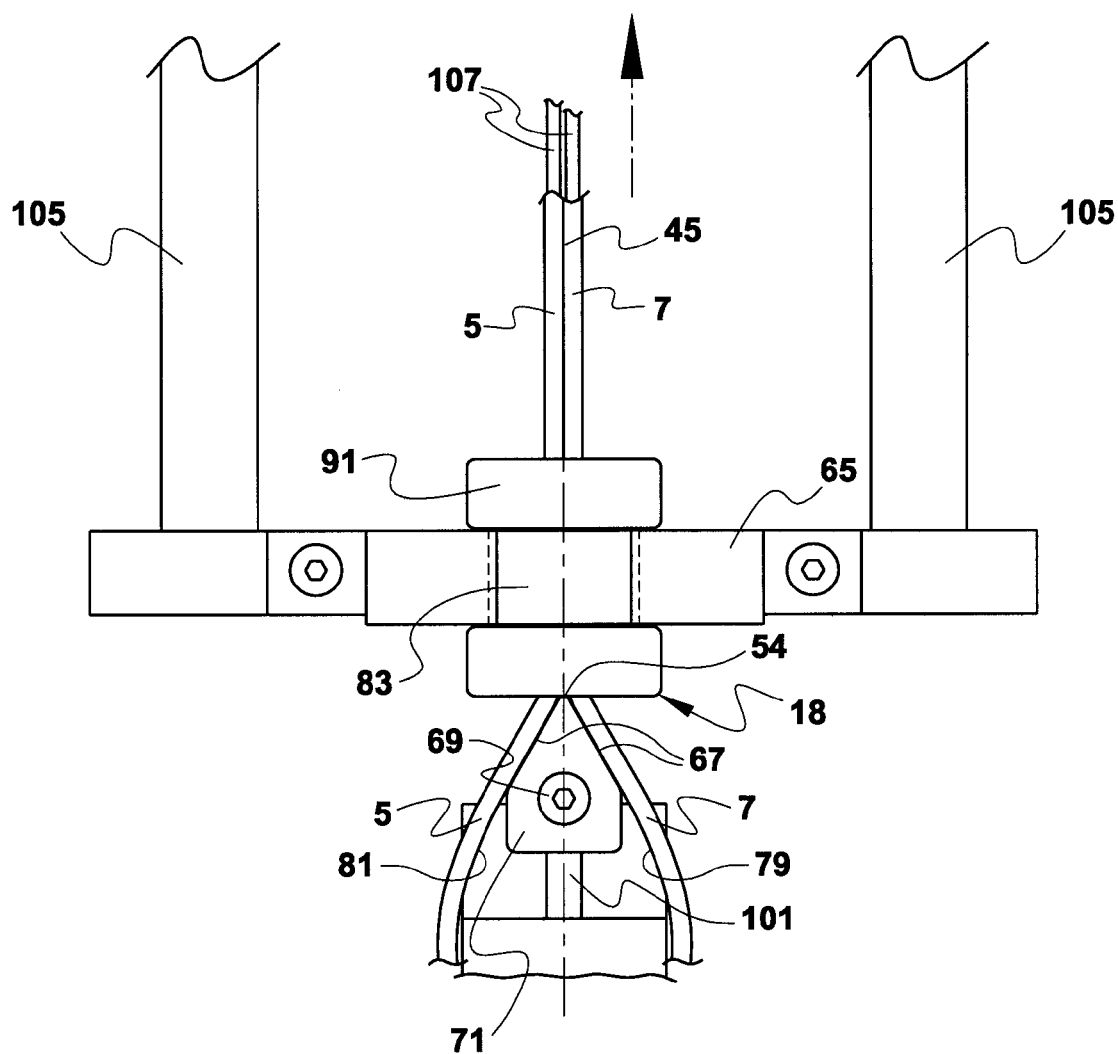
FIG. 10 illustrates a partial elevational view of a portion of the tube joining assembly in which a portion of the catheter tubes are being joined together during the catheter manufacturing method described herein.

In other exemplary aspects, other methods and sealing means can be used to seal the ends of the catheter tubes 5, 7, such as, but not limited to the placement of at least one base mandrel 107 into at least a portion of at least one of the catheter tube 5, 7 lumens, as illustrated in FIG. 10. The base mandrels 107 are attached to base plate 80 of the tube joining assembly 73, described below. The mandrels 107 are used to keep the catheter tubes 5, 7 in place during the tube joining process described herein, while the opposite ends of the catheter tubes 5, 7 are sealed to maintain air pressure in the tubes 5, 7. In one aspect, the mandrel 107 can provide support for the catheter tube lumens. In one exemplary aspect, the sealing means or mandrel 107 can be a wire mandrel. In another aspect, the mandrel 107 can be a stainless steel hypo tube. In one exemplary aspect, at least a portion of the at least one catheter tube 5, 7 can be slid onto at least one holding mandrel 107, such that the at least one mandrel 107 can extend through substantially the entire length of at least one lumen of the catheter tubes 5, 7.

Figure 8:
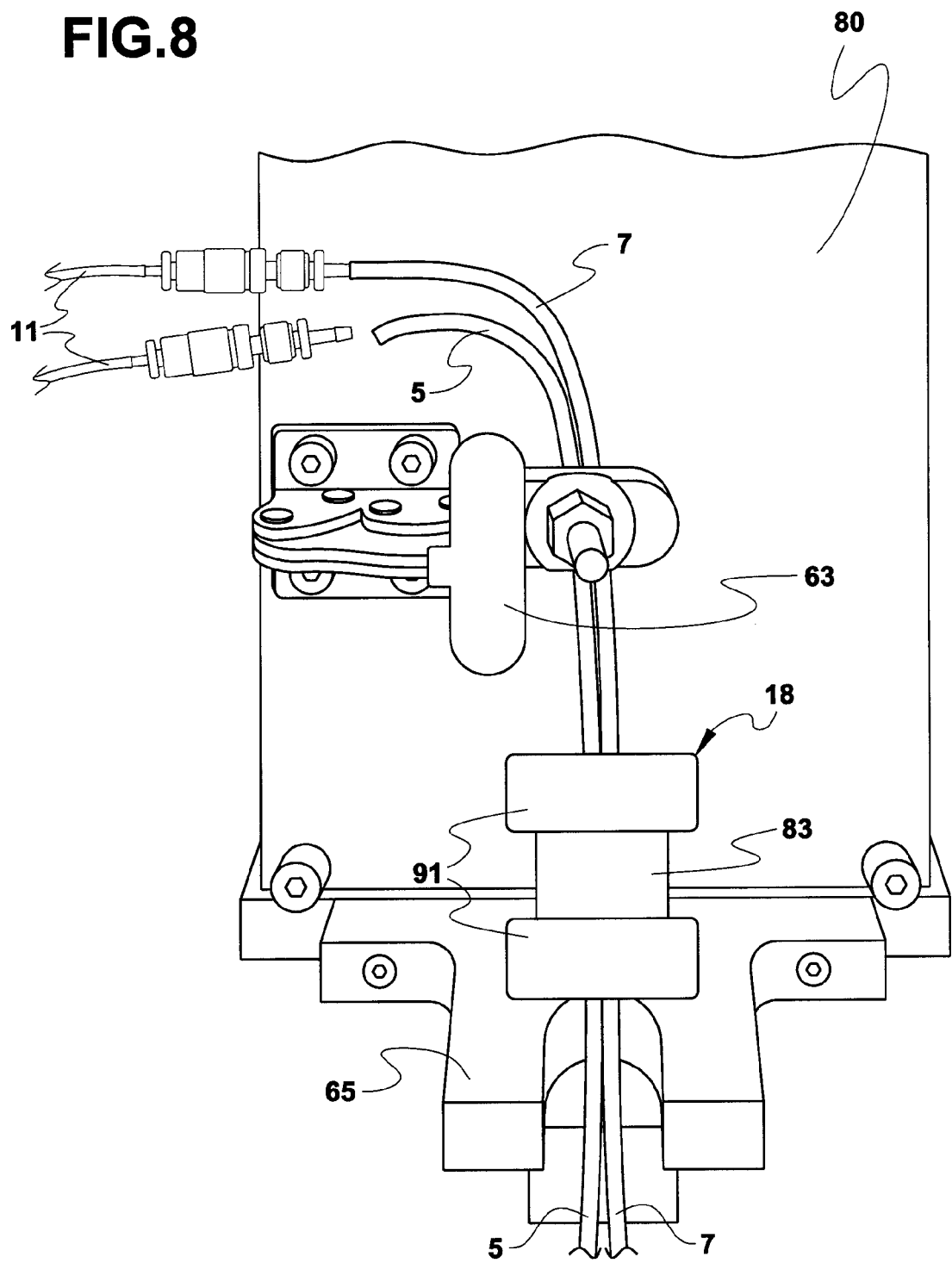
FIG. 8 illustrates a partial elevational view of one end of at least a portion of the catheter shaft of FIG. 1 being connected to a portion of the tube joining assembly for the catheter manufacturing process described herein.

Alternatively, at least a portion of one end of at least one of the catheter tubes 5, 7 can be clamped shut using a different type of sealing means, such as clamp 63, as illustrated in FIG. 8. In one aspect, at least a portion of the clamp 63 can be placed around at least a portion of the outer surface of at least one of catheter tubes 5, 7 to hold the at least two tubes 5, 7 vertically in place during the manufacturing process. Other methods, such as, but not limited to, folding, clipping, or otherwise binding at least a portion of one of the ends of at least one of the catheter tubes 5, 7 shut can also be used. Optionally, this step of sealing the catheter tubes 5, 7 can be omitted in some catheter embodiments. In one aspect, barbed fittings from an air supply or lumen pressurizing tube can be inserted into at least one of the remaining open lumens of at least one of the catheter tubes 5, 7 opposite the sealed lumen portion of each of catheter tubes 5, 7. In one aspect, the barbed fittings can be positioned therein the top of a luer connector that is defined therein the top of the air supply or lumen pressurizing tube. It is important to seal the catheter tubes 5, 7 in order to maintain the original shape and size of the catheter tubes and lumens during the heat bonding process described herein.

Figure 7A:
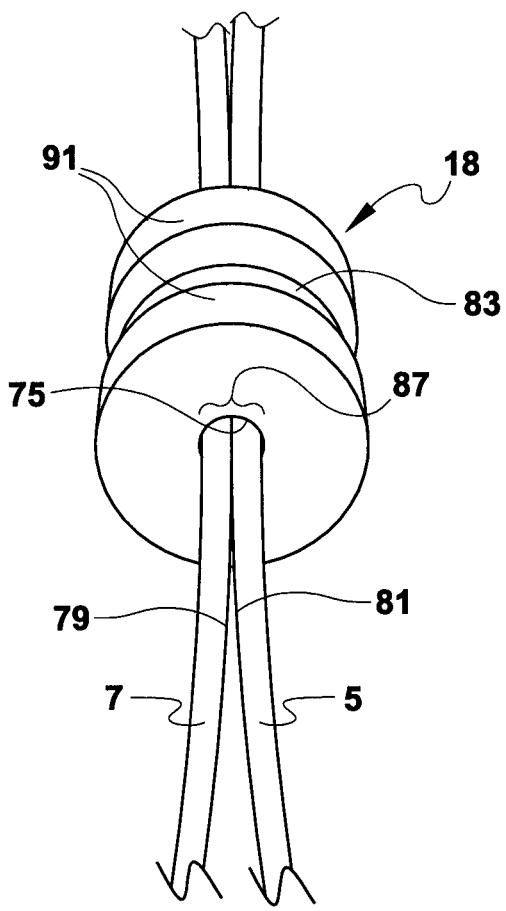
FIG. 7A illustrates a partial perspective view of a die in which at least a portion of the catheter tubes of the catheter of FIG. 1 are inserted for the catheter manufacturing process described herein.
Figure 7B:
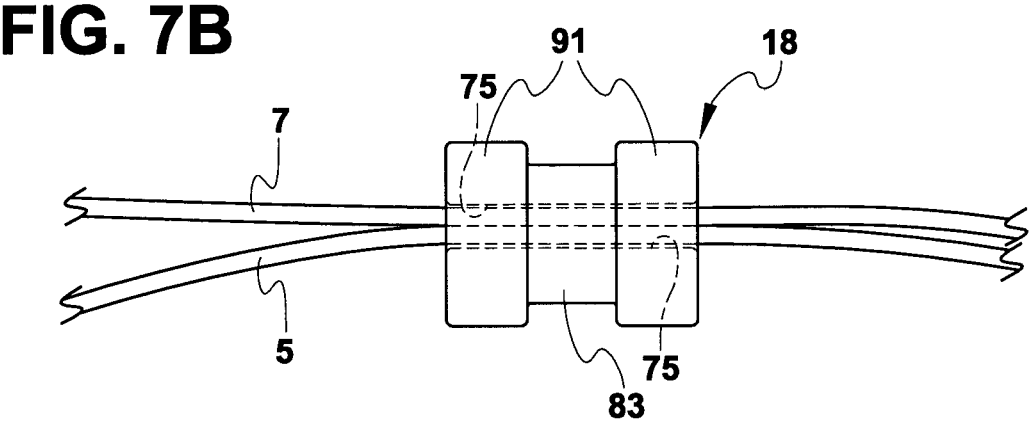
FIG. 7B illustrates a partial elevational view of the die of FIG. 7A in which at least a portion of the catheter tubes of FIG. 1 are inserted for the catheter manufacturing process described herein.

Referring to FIGS. 7A and 7B, after at least one of the ends of each of the catheter tubes 5, 7 are sealed off to maintain pressure within the catheter tubes 5, 7, as described above, at least a portion of the catheter tubes 5, 7 are threaded through a tube holding means. In one aspect, the tube holding means can comprise a joining die 18. In one aspect, the die 18 can have a center orifice 75 through which at least a portion of the catheter tubes 5, 7 are positioned. In one aspect, at least a portion of each of the catheter tubes 5, 7 are juxtaposed with each other in a coextended arrangement such that a portion of the inner surfaces 79, 81 of the catheter 5, 7 are internally opposed to one another. In one aspect, at least a portion of the surface of catheter tube 5 is in contact with at least a portion of the surface of catheter tube 7.

In one exemplary aspect, the die orifice 75 can have a diameter of between about 0.100 inches and about 0.200 inches. More particularly, the die orifice 75 can have a diameter of approximately 0.186 inches, although other dimensions are contemplated. In another exemplary aspect, the die orifice 75 can have a diameter of approximately 0.187 inches. In one aspect, the die holder 18 can comprise a cylinder 83 and a set of opposing flanges 91 positioned on each side of the cylinder 83. In one aspect, the cylinder 83 can have a diameter of approximately 0.75 inches. In one aspect the outer flanges 91 can each have a diameter of about 1 inch and a height or thickness of approximately 0.375 inches, although other dimensions are contemplated. In one exemplary aspect, the die 18 can have a total height of approximately 1.25 inches. In one exemplary aspect, the die can comprise a chamfer 87 that is approximately 0.208 inches in diameter. In this aspect, the chamfer 87 can have a beveled edge that is designed for selective receipt of at least two catheter tubes 5, 7 of various diameters or sizes.

The die orifice diameter and the chamfer diameter are sized to accommodate catheter tubes 5, 7 to produce a finished catheter shaft having an outer diameter of about 0.207 inches. In one exemplary aspect, as one of ordinary skill in the art will appreciate, the size of the die 18, along with the overall shape of the die 18 or the die orifice 75 size can be adjusted to allow for different sized catheter tubes. The die can accommodate a 15 French or 16 French catheter. It is contemplated that different sized catheter tubes can also be accommodated, depending on the size of the die used. In one aspect, the joining die 18 can be made of Teflon.

In another exemplary aspect, the die 18 can be made of other materials such as, but not limited to, Delrin or any other type of smooth material. The die 18 described herein is useful for exerting pressure on a portion of each of the inner surfaces 79, 81 of catheter tubes 5, 7 such that the surfaces 79, 81 are compressed together against each other during the manufacturing process described herein.

As illustrated in FIG. 8, after at least a portion of the tubes 5, 7 are sealed and placed inside of the die orifice 75, the air in the lumens 36, 39 is then pressurized. To accomplish this, at least a portion of the tubes 5, 7 can be connected to at least one pressure source. In one aspect, the at least one pressure source can be connected to at least one air line 11. In one aspect, the pressure source can be connected to two air lines 11. Each of the air line 11 can be attached to an open end of each of the catheter tubes 5, 7. In one exemplary aspect, the air lines 11 can be set to have an air pressure of between about 2 psi and about 4 psi. In one exemplary aspect, the air lines 11 can be set to have an air pressure of about 2 psi. In one exemplary aspect, the air lines 11 can be set to have an air pressure of about 0.5 psi in order to create a pressure of about 2 psi within the sealed catheter tubes 5, 7. This allows pressure to be sealed within the tubes 5, 7 during the manufacturing process and allows the inner surfaces 79, 81 of the catheter tubes 5, 7 to maintain a uniform configuration within the tube joining die 18 during the manufacturing process. The pressure that is infused into the lumens of the at least two catheter tubes 5, 7 from the air lines 11 can also help to keep the catheter lumen dimensions intact while heat is applied to at least a portion of the catheter tubes. Although air lines 11 are described herein, other types of pressure sources and air pressurizing systems could be used to pressurize the lumens 36, 39 of catheter tubes 5, 7.

Figure 9:
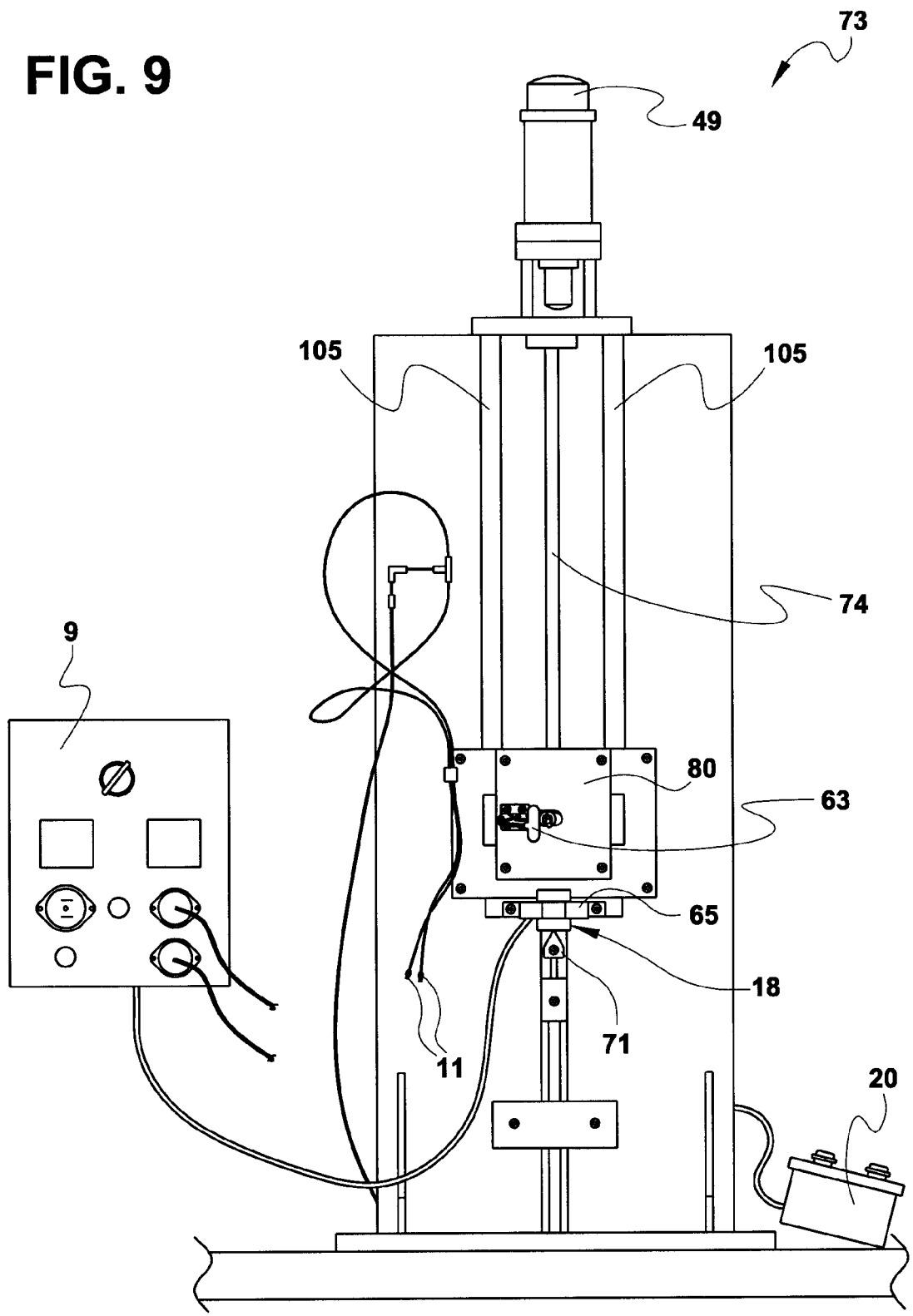
FIG. 9 illustrates a partial elevational view of the tube joining assembly used in the catheter manufacturing process described herein.

After at least a portion of the catheter tubes 5, 7 are placed within a portion of the tube holding means or die 18, the die 18 is placed in and secured to a die holder 65 of a tube joining assembly 73, illustrated in FIG. 9. In one aspect, the tube joining assembly 73 can have any number of different configurations, such as, but not limited to the configuration illustrated in FIG. 9. One of ordinary skill in the art will recognize that other types of tube joining assembly machines could be built and used in the manufacturing process described herein. In one exemplary aspect, at least a portion of the catheter tubes 5, 7 are then secured to at least a portion of the tube joining assembly 73. The assembly 73 can comprise tube holding fixture or clamp 63, a tube holding means or die 18, air lines 11 that are connected to a pressure source, a temperature controller 9, a motor 49, a vertical pull 74, at least one vertical pull rod 105, a vertical back plate 80, a heating means such as, but not limited to, a heating block or roller 71, and a power/direction controller 20.

Referring to FIG. 10, at least a portion of the heating means or heating block 71 can be used to heat at least a portion of catheter tubes 5, 7 before joining the catheter tubes 5, 7 together in the die 18. In one aspect, at least a portion of the inner surfaces 79, 81 of the at least two catheter tubes 5, 7 can be heated using the heating block 71. The heating block 71 can be made of brass, although any suitable heat-conducting metal can be used. The heating block 71 can comprise at least one outer surface 67. In one exemplary aspect, the heating block 71 can have two outer angled surfaces 67 that form a longitudinal edge 54. The outer angled surfaces 67 can be substantially equally dimensioned. In one exemplary aspect, the two angled surfaces 67 can be planar. In yet another embodiment, the heating block 71 can have any suitable shape to allow at least a portion of a surface one catheter tubes 5, 7 to become heated before being joined together in the die 18.

Catheters with various cross-sectional lumen configurations can be produced using the manufacturing process described herein, depending on the shape of the heating block 71 used, as illustrated in FIGS. 2A through 3C. In one optional embodiment, at least a portion of the heating block 71 can be covered with Teflon tape. At least a portion of surface 67 can be covered by Teflon tape or fabric. Teflon faced fabric can be used to create a non-stick surface over at least a portion of the outer surface 67 of the heating block 71. Any type of non-stick surface, other than Teflon non-stick tape, can be used on at least a portion of the outer surface 67 of the heating block 71. Although the heating means 71 is described herein as having a square or triangular configuration, in one exemplary embodiment, the heating means 71 can be in the shape of a roller.

In one exemplary aspect, the temperature of the heated block 71 can be controlled by a temperature controller 9, illustrated in FIG. 9. The temperature controller 9 can be set at a temperature of between about 300° F. and about 450° F. The temperature controller can be set to a temperature of between about 400° F. and about 450° F. The temperature can be set to between about 410° F. and about 440° F. More particularly, the temperature of the heating block 71 can be set to about 435° F. One of ordinary skill in the art will recognize that any suitable practical range for the motor speed of the motor/controller and/or the temperature of the heating block 71 can be established for the catheter manufacturing process described herein. In one aspect, any of the parameters described herein can be set or adjusted during the manufacturing process described herein or during process operational qualification, depending on the tubing lot or on the level of heat bonding desired. In one aspect, such parameters can include, but are not limited to, temperature of the heating block 71, shape of the heating block 71, draw speed, tube material and other characteristics, such as dimensions, lumen configuration, sidewall thickness, air pressure, and die pressure. For example, some tube materials can require higher temperatures to achieve effective bonding. In another exemplary aspect, the temperature of the temperature controller 9 can be varied so as to allow variations in the bond strength between the inner surfaces 79, 81 of the at least two catheter tubes 5, 7.

At least a portion of the surfaces of the catheter tubes 5, 7 can be placed on at least a portion of a surface 67 of the heating block 71. More particularly, in one exemplary aspect, at least a portion of the inner surfaces 79, 81 of the catheter tubes 5, 7 can be placed on at least a portion of the surface 67 of the heating block 71. More particularly, in one aspect, during the heat bonding process described herein, at least a portion of the catheter surfaces can lie or abut against at least a portion of the angled surfaces 67 of the heating block 71. At least a portion of the surfaces of the catheter tubes 5, 7 can be uniformly heated as they are pulled over a portion of surface 67 because the surface 67 can comprise a planar surface that can allow the catheter tube 5, 7 surfaces to have substantially equal contact with at least a portion of the catheter 5, 7 surfaces.

In one aspect the controller 49, illustrated in FIG. 9, of the tube joining assembly 73 can control the speed at which the surfaces of the tubing 5, 7 are pulled across at least a portion of the surface 67 of the heating block 71. In one exemplary aspect, the motor or speed controller 49 can be set at a speed of between about 10 cm/minute and about 30 cm/minute. In another exemplary aspect, the motor/speed controller 49 can be set at a speed of between about 15 cm/minute (approximately 4.5 on a dial) and about 25 cm/minute. In yet another exemplary aspect, the motor/speed controller 49 can be set at a speed of about 24 cm/minute. In one aspect, when the motor/speed controller 49 is activated, the catheter tubes 5, 7 can be moved vertically from the die 18 upward toward the motor/controller 49. In one exemplary aspect, the tubing fixture or clamp 63 or the mandrels 107 can be attached to face plate 80. In one aspect, mandrels 107 or the holding fixture or clamp 63, as described above, can hold at least a portion of the tubes 5, 7 vertically in place as the vertical pull 74, which is attached to the face plate 80, is moved vertically upward toward the controller 49. When the vertical pull 74 moves upward, the catheter tubes 5, 7 inside of the die 18 are pulled vertically upward toward motor 49.

As the catheter tubes 5, 7 are pulled upward toward the motor or speed controller 49 of the tube joining assembly 73, the orifice 75 of the joining die 18 is configured to align at least a portion of the inner surfaces 79, 81 of the two catheter tubes 5, 7 together and to generate a force between a portion of the inner surfaces 79, 81 during heating of the catheter tubes. In one exemplary aspect, if the catheter tubes 5, 7 illustrated in the embodiment of FIG. 2C are used in the manufacturing process described herein, as described above, the orifice 75 of the die 18 can exert pressure on a portion of each of the catheter tubes 5, 7 such that the opposed inner surfaces 79, 81 of the two catheter tubes 5, 7 are pressed together, and the convex shape of the tubes 5, 7 can become concave or flat. In one aspect, the convex joining surfaces 79, 81 can be dimensioned to ensure that at least a portion of each of the inner surfaces 79, 81 are in contact with a portion of heating block 71 and with each other during the manufacturing process. After at least a portion of inner surfaces 79, 81 are bonded together using the manufacturing process described herein, and compressed by die 18, at least a portion of the joined catheter tubes 5, 7 can be cooled by the die 18. The die 18 can act as a cooling means to help cool the joined catheter tubes 5, 7 by transferring heat from the tubing 5, 7 to the die 18, thereby acting as a sufficient heat sink to protect the outer surfaces 43, 47 of the catheter tubes 5, 7 from heat.

A sufficient heat fusion bond can be formed between at least a portion of catheter tubes 5, 7 by the catheter manufacturing process described herein. More particularly, in one aspect, a sufficient heat fusion bond can be formed between at least a portion of the two inner surfaces 79, 81 of the catheter tubes 5, 7 to form a unitary septum 77, as illustrated in FIGS. 2A, 5B, and 5C. In one aspect, after at least a portion of the inner surfaces 79, 81 of each of the catheter tubes 5, 7 are heated across a portion of the surface 67 of the heating block 71, at least a portion of the two catheter tube 5, 7 surfaces can heat bond or fuse together.

Over-heating of any portion of the surfaces of tubes 5, 7 can cause excessive deformation of the catheter tubes 5, 7 as they are drawn across a portion of the surface 67 of the heating block 71 and through the joining die 18. This could potentially lead to leaking (inter-lumen communication or external). In one aspect, the manufacturing process further involves providing a means for controlling the time of heat exposure of at least a portion of the inner surfaces 79, 81 of the catheter tubes 5, 7 to a portion of the surface 67 of the heating block 71. In one aspect, the means for controlling the time of heat exposure can prevent over-heating, uneven heating, and leaking from occurring. The means for controlling the time of heat exposure can be a controller 49. The controller 49 can control at least the draw speed, which controls the speed at which the inner surfaces 79, 81 of the catheter tubes 5, 7 are pulled across a portion of the surface 67 of the heating block 71, and the temperature of the heating block 71. As at least a portion of the at least two catheter tubes 5, 7 are pulled upward through the die 18, at least a portion of the inner surfaces 79, 81 of the catheter tubes 5, 7 can be uniformly heated.

In one aspect, certain heat-bonding zones can be created along selected portions of the inner surfaces 79, 81 of the catheter tubes 5, 7 by altering the speed of the heat-bonding process at different points along the catheter tube surfaces. In one aspect, this can be accomplished by altering the draw speed, as described above. The at least two catheter tubes 5, 7 can be heated at varying speeds along various portions of the at least two catheter tubes 5, 7. The at least two catheter tubes 5, 7 can be heated more quickly along at least a portion of the catheter tube surfaces compared to other portions of the catheter tube surfaces. In one exemplary aspect, at least a portion of the catheter tube surfaces can be effectively heated, and at least a portion of the catheter tube surfaces can be heated less effectively or not at all, depending on the desired outcome. For example, several parameters could be changed to affect the strength of the heat fusion bond between catheter tubes 5, 7. In one example, the faster the tubes 5, 7 are heated over the heating block 71, the less the tubes 5, 7 are melted and the weaker the bond created between the tubes 5, 7. The more slowly the tubes are heated over the heating block 71, the greater the melting of the inner surfaces 79, 81 and the stronger the bond strength between the inner surfaces 79, 81 of the catheter tubes 5, 7.

The manufacturing process described herein can be used to produce split tip catheters with alternating or segmented heat fusion bonds having any of the distal tip configurations illustrated in FIGS. 1 through 5C by alternating the contact time of at least a portion of the inner surface 79, 81 of each catheter tube 5, 7 with the heating block 71 and/or Teflon tape that can cover the heating block 71. In one exemplary aspect, at least a portion of the inner surfaces 79, 81 of the catheter tubes 5, 7 can contact at least a portion of the surface 67 of the heated block 71 for approximately 1-3 mm, followed by no contact with the Teflon-covered surface 67 of the heated surface 71 for 1-3 mm and so forth, in an alternating pattern.

The temperature of the heating block 71 can be adjusted, depending on the desired tack of the catheter tubes 5, 7. For example, the temperature of the heating block 71 can be lowered to reduce the tack between the catheter inner surfaces 79, 81 to allow for the catheter tubes to be pulled apart more easily, such as desired in a splittable catheter configuration, illustrated in FIG. 5A. In yet another aspect, the amount of contact of a portion of the inner surfaces 79, 81 of the catheter tubes 5, 7 with at least a portion of the outer surface 67 of the heating block 71 can be controlled and/or altered to reduce the force that would be needed to allow at least a portion of the catheter tubes 5, 7 to be split apart. In yet another aspect, the following parameters can be changed to alter the strength and the location of the heat-bonding between a portion of the surfaces of the two catheter tubes 5, 7: the temperature of the heating block 71, the draw speed, which controls the speed at which the vertical pull 74 ascends toward the motor/controller 49, can be changed, and the air pressure or die pressure. Altering these parameters can affect the splittability of the catheter tubes.

Figure 11:
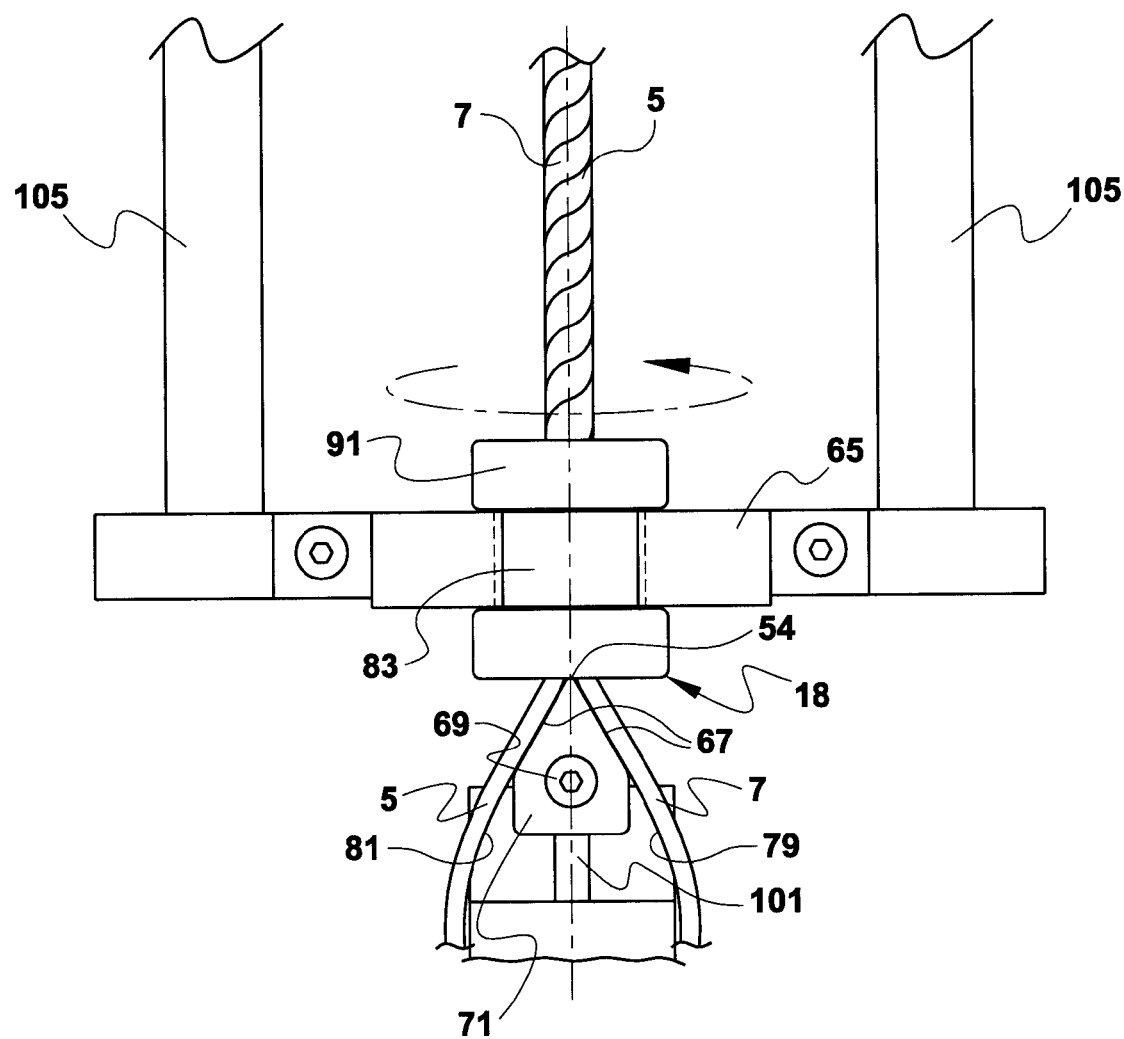
FIG. 11 illustrates a partial elevational view of a section of the tube joining assembly in which a portion of the catheter tubes are being wound together during the catheter manufacturing method described herein.

In one aspect, after the motor 49 is activated, the power controller 20 can be used to move the face plate 80 upward. As the face plate 80 moves upward, at least one portion of the inner surfaces 79, 81 of the tubes 5, 7 can be moved across the at least one surface 67 of the heating block 71 and through the orifice 75 of the joining die 18 as the heating block 71 is advanced up against the catheter tubes 5, 7, as illustrated in FIGS. 10 and 11. As the catheter tubes 5, 7 are moved vertically, the die holder 65 remains stationary. As illustrated in FIGS. 10 and 11, the heating block 71 can be a unitary block. In yet another aspect, the heating block 71 can comprise a heating element 69 that is positioned therein substantially the entire length of the heating block 71. In one aspect, heating element 69 can be positioned substantially in a center portion of the heating block 71 and can provide uniform heat dispersion throughout the heating block 71. The heating block 71 can comprise an extending wall 101 that that can be used to snap-lock at least a portion of the heating block 71 with the tube joining assembly 73. In one exemplary aspect, the extending wall 101 can form an interference fit with a slot (not shown) in the tube joining assembly 73. In one aspect the snap-lock interference fit that is created between the extending wall 101 and the tube joining assembly 73 can ensure that heating block 71 is secured to a portion of the assembly 73 during the manufacturing process. In one aspect, the extending wall 101 can be held in place with a set screw. In one exemplary embodiment, the heating block 71 can be adjustable such that during the manufacturing process, the heating block 71 can move toward or away from the die 18.

In one aspect, at least a portion of the inner surfaces 79, 81 of the catheter tubes 5, 7 are heated as they are passed along at least a portion of the outer surface 67 of the heating block 71, after which they are joined together, as shown by interface 45 (also illustrated in FIGS. 1, 2A, and 3A-5C), beginning at a point just above longitudinal edge 54, where the two angled equally dimensioned surfaces 67 of the heating block 71 meet. Thus, in one aspect, at least a portion of inner surface 79 of catheter tube 7 can be joined to at least a portion of inner opposing surface 81 of catheter tube 5. In one aspect, at least a portion of inner surface 79 can be releasably or permanently joined to at least a portion of inner surface 81. As the tubes 5, 7 are vertically pulled upward toward the motor/controller 49, they are joined together to form a unitary catheter shaft 3 with a cross section as illustrated in FIG. 2A or 5A-5B, for example. In one aspect, because only at least a portion of the inner surfaces 79, 81 of the catheter tubes are heated by the heating block 71, the catheter shaft 3 can retain its overall profile shape as the tubes are pulled through the joining die 18. Tubes 5, 7 can be held and joined together by internally opposed inner surfaces 79, 81.

At least one wire can be fed through at least a portion of the heated block 71. Although not illustrated, the heating block 71 can comprise at least one receiving means such as, but not limited to, a hole, a channel, or a bore. In one aspect, the receiving means can be defined therein at least a portion of the heated block 71. The receiving means can be positioned in the heating block 71 between two angled surfaces 67 such that the receiving means extends substantially entirely through the heating block 71 from one portion of the outer surface 67 of the heating block 71 to another portion of the outer surface 67 of the heating block. The receiving means can extend substantially vertically through at least a portion of the heating block 71. In one exemplary aspect, the receiving means can comprise more than one hole or channel that can be positioned therein at least a portion of the heating block 71. The receiving means can be capable of receiving at least one additive, such as, but not limited to a wire, an electrode, and radiopaque material. In one exemplary aspect, at least one wire could be fed through the receiving means and drawn up vertically through the receiving means between the catheter tubes 5, 7 such that as the catheter tubes 5, 7 are being heat bonded together, the at least one additive can become embedded in a portion of at least one surface of catheter tubes 5, 7, as described herein.

The catheter manufacturing process described herein can also be used to produce triple lumen catheters, as described above and exemplary end views of which are illustrated in FIGS. 3A through 3C. This can be done by placing a mandrel or tube between two catheter tubes 5, 7. In one aspect, the mandrel or tube can be defined therein at least a portion of a center of the tube joining assembly 73. Alternatively, in one aspect, heat can be applied to at least a portion of the inner surfaces 79, 81 of each catheter tube 5, 7, such that only a portion of the inner surfaces 79, 81 are heated, thereby creating a third lumen between the two catheter tubes 5, 7, as illustrated in FIG. 3A. In yet another aspect, the shape of the heating block 71 can be configured to produce a catheter having third lumen.

The catheter heat bonding process described herein is beneficial because it can prevent catheter tube material from melting or bleeding over the edges of at least a portion of each of the catheter tubes 5, 7. This can be illustrated, in one aspect, by using two catheter tubes 5, 7 of different colors during the manufacturing process, such as a white tube and a blue tube, as described in U.S. patent application Ser. No. 12/648,169, which is incorporated herein by reference in its entirety. In this aspect, the two catheter tubes 5, 7 can be fixed to each other by bonding at least a portion of the inner surfaces 79, 81 of the catheter tubes without the use of any additional sleeve or similar device or method. In one aspect, during the catheter manufacturing process described herein, no heat is applied to the outer surfaces 43, 47 of the catheter tubes 5, 7, except for negligible heat convection in the region of the heating block 71. As at least a portion of each of the catheter tube inner surfaces 79, 81 are heated, at least a portion of the inner surfaces 79, 81 become softer and stick together. In one aspect, during the step of joining at least a portion of each of the catheter tubes 5, 7 together, the two catheter tubes 5, 7 are heat bonded or fused directly to each other to form a unitary catheter shaft 3 configuration. During heating of the catheter tubes 5, 7 together, the cross-sectional profile of the catheter tubes 5, 7 is maintained, and the catheter is not damaged as it is pulled through the joining die 18.

As illustrated in FIG. 11, another embodiment of the catheter manufacturing method is illustrated in which after at least a portion of the catheter tubes 5, 7 are heat bonded together, they are then rotated together in a clockwise or counterclockwise direction, as indicated by the arrow, as the catheter tubes 5, 7 move vertically upward toward the motor 49, as described above, to form an exemplary catheter shaft 3 having a first catheter tube 5 and a second catheter tube 7. As the tubes 5, 7 are rotated or twisted during the manufacturing process, at least a portion of the first tube 5 forms a first substantially spiral shape, and at least a portion of the second tube 7 forms a substantially spiral shape. The spiral shaped first tube 5 and the spiral shaped second tube 7 can extend along a longitudinal axis between the proximal end and the distal end of the catheter shaft 3 in a cylindrical shape. In one aspect, as the tubes 5, 7 are rotated, at least a portion of each of tubes 5, 7 become axially overlapped in nested relation to each other.

In one aspect, the speed of the clockwise or counterclockwise rotation can be controlled independently of the draw speed, described herein. In one aspect, the speed at which the die 18 rotates can be altered to be faster or slower using the motor/controller 49, depending on the desired winding pitch of the catheter tubes 5, 7. In another aspect, the die 18 can be kept stationary while the at least two catheter tubes 5, 7 can be spirally wound together as they are pulled upward by the vertical pull 74. In another aspect, the catheter tubes 5, 7 can be wound together such that they have varying winding pitches at different portions along the catheter shaft 3. This process can produce tightly wound spiral catheter tubes or loosely spiraled catheter tubes. In one aspect, it can be desirable to use at least two catheter tubes with different durometers, colors, or materials to create a catheter shaft 3 having spiral shaped tubes.

In one aspect, a catheter shaft 3 having catheter tubes with spiral shapes is desirable because it can allow for more strategic placement within a patient's body. This in turn, can allow for more strategic delivery of contrast agents or therapeutic or medicinal treatments.

In another aspect, the increased therapeutic placement can allow for more effective treatment of fibrin sheaths that can build up along the catheter shaft. In yet another aspect, a catheter shaft with spiral shaped tubes can be desirable to prevent occlusion of a particular catheter lumen as a result of the particular placement of the catheter within the patient. In one aspect, triple lumen catheters having spiral shaped catheter tubes, in particular, can provide performance which is superior to that of non-spiraled triple lumen catheters. For example, if side holes are present in the catheter shaft 3, and the holes are arranged in a single line, the side holes can press up against the inside of a vessel wall such that they can become occluded. However, catheter shafts having spiral shaped tubes with staggered side hole positions can prevent catheter holes from becoming occluded. A spiral shaped catheter can also provide additional resistance to kinking.

In one aspect, other types of heat-bonding mechanisms could be used in the heat-bonding process described herein. In one aspect, other heat sources such as hot air, radiant infrared, contact and non-contact heating elements can be used to confer heat to at least a portion of the catheter surfaces, while leaving at least a portion of the catheter tube surfaces untouched and unaffected by any heating process. Thus, in one aspect, at least a portion of the catheter tube surfaces can be joined by any suitable heat-sealing process. In one aspect, such heat-sealing processes can involve creating at least one lumen profile and heat-sealing the lumen profiles together to form at least one lumen of a catheter shaft.

Figure 12:
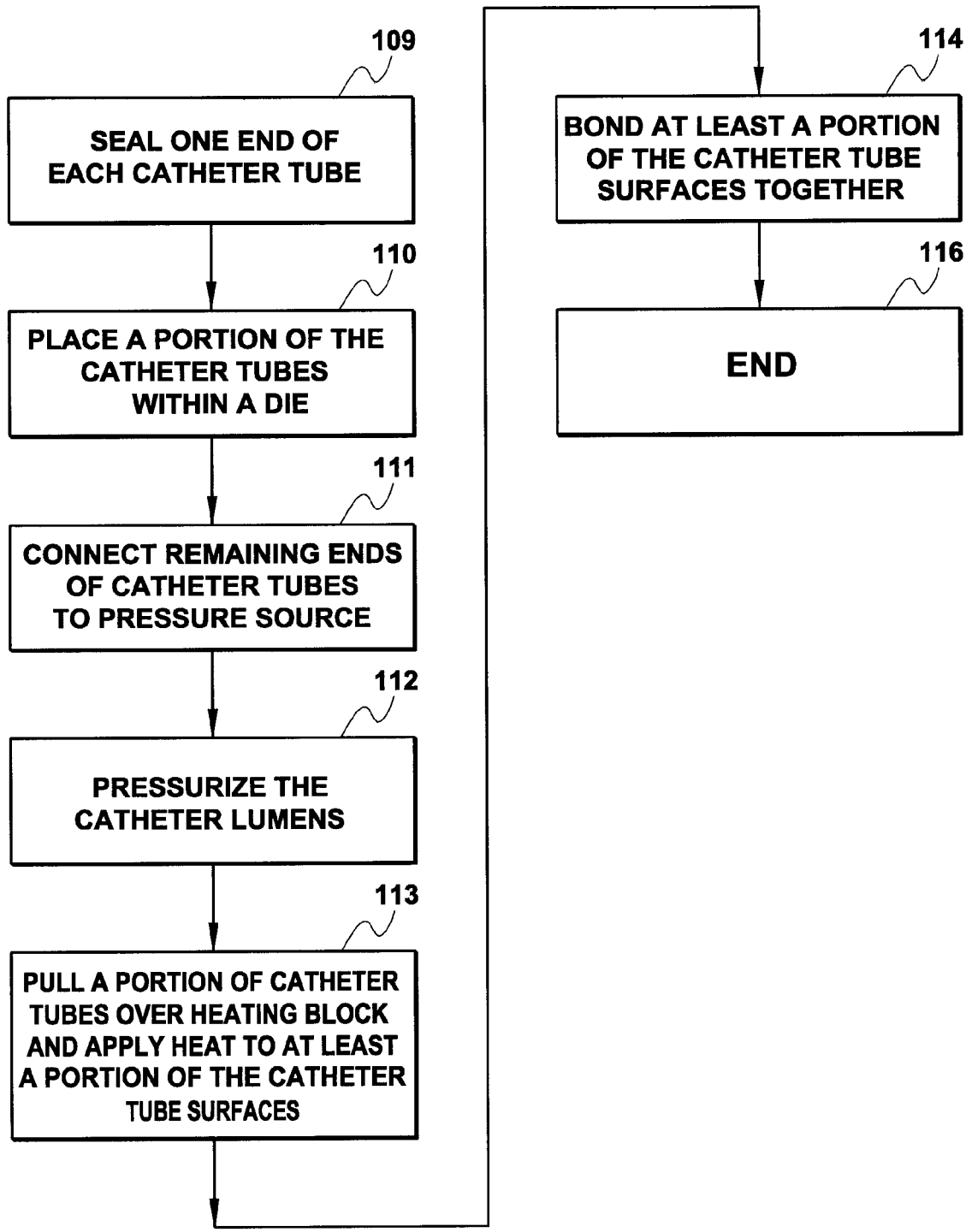
FIG. 12 illustrates a flow diagram of the catheter manufacturing method disclosed herein.

In one aspect, the method of manufacturing described herein is also illustrated in the flow diagram of FIG. 12. The manufacturing process, which is described in detail herein, involves providing a plurality of tubes, each tube having a first end, a second end, at least one lumen extending longitudinally through at least a portion of each tube, and at least one surface; sealing at least one end of each catheter tube; placing a portion of the catheter tubes within a die, connecting the remaining ends of the catheter tubes to a pressure source, pressurizing the catheter lumens, pulling a portion of the catheter tubes over a heating block and applying heat to selectively heat at least a portion of at least one surface (the inner surface) of at least one tube of the plurality of tubes; and contacting the selectively heated portion of at least the first tube with at least a portion of a second tube to form a multi-lumen catheter shaft that is bonded or joined together along at least a portion of the length of the catheter shaft. In another embodiment, the inner surfaces of both catheter tubes could be simultaneously heated and the selectively heated portions of the catheter tubes could then be joined or fused together.

In one aspect, the manufacturing process described herein can be automated or computerized such that the process is capable of heating multiple sets of catheter tubes at a time, instead of just a single set of catheter tubes at a time. In one exemplary aspect, a "set" of tubes is defined herein to mean at least two catheter tubes 5, 7. In one exemplary aspect, the manufacturing process described herein can heat-bond up to five sets of catheter tubes at one time. One of ordinary skill will recognize that more than five sets of catheter tubes can be heat-bonded using the manufacturing process described herein. In one aspect, the manufacturing process described herein may involve a combination of user-operated and automated steps. During this process, the settings for the catheter manufacturing process can be chosen and verified to produce the desired catheter. In one aspect the settings can include the motor speed and/or the temperature of the heating block, the catheter tubing length, the heater delay, and/or the heater reset.

In one aspect, after the completion of the heating cycle or heat bonding of the catheter tubes 5, 7, the die 18, vertical plate 80, and bonded tubes 5, 7 are removed from the machine 73. In one aspect, the tubing is then removed from the mandrels 107 and the die 18, and the clamps (if any) and barb fittings from the tubing are then removed. The catheter tubes 5, 7 are then inspected and cut to length.

After the catheter manufacturing process is completed, as described above, the catheter can then be molded, as is known in the art. This process can involve injection molding the extension legs to the catheter shaft and creating a through lumen from the extension legs to the catheter shaft and curve-baking the catheter shaft in order to create a pre-curved catheter shaft. The catheter tip can then be then formed by skiving the venous and arterial lumen tips at a desired angle, using processes known in the art. Clamps can then be slid along the catheter shaft, and the appropriate luer hub can then be attached to the catheter using a chemical or adhesive bond. A cuff and suture wing can then be attached.

The catheter manufacturing process described herein has several benefits. The manufacturing process herein eliminates the need for additional layers, sleeves, coatings, adhesives, membranes, breakable ultrasonic welds, or thin polymeric breakable layers. The process disclosed herein is advantageous because the process can take approximately under one minute to complete, compared to longer processes, such as the platen process, which can take approximately five minutes to complete. In one exemplary aspect, a few simple parameters, such as air pressure, temperature, and temperature locations can be adjusted to produce different lumen configurations rather easily without having to use complicated, messy, or hazardous extrusions, chemical or solvent bonding processes, or platen molds. In one aspect, different types of tubing can be used, such as, but not limited to, durometer, material, colors, or different sizes of tubing, such as flat, round, or square tubing to produce different catheter shaft and lumen configurations. In one aspect, up to four pieces of tubing can be heat-bonded together using the manufacturing process described herein. In yet another embodiment of this invention, different solid or partially solid pieces of plastic materials can be joined together. For example, in one embodiment, different shapes, sizes, or compositions of plastic components can be joined together using the process disclosed herein to form different plastic components of various compositions and sizes. Such pieces of plastic can be solid tubes of plastic material or they can be plastic-type pieces that have lumens within the pieces.

The manufacturing process disclosed herein is beneficial because at least a portion of at least one catheter tube surface is heated across a Teflon-covered surface 67 of the heating block 71, the remaining portions of the catheter tube surfaces remain unaffected by heat, and therefore they can maintain a smooth surface finish. This prevents the originally extruded surface finishes from being compromised throughout the heat-bonding process described herein. This method also avoids the need for an outer layer or other type of sheath to be placed around the catheter, thereby minimizing overall outer diameter of the catheter shaft. The method described herein allows heat to be focused on at least a portion of the at least two catheter tubes such that a strong, reliable bond is created between the at least two catheter tubes, without heat affecting the outer surface of the finished unitary catheter shaft. In one aspect, heat can be provided only along at least a portion of the catheter tube surface where it is needed. In another aspect, the portions of the catheter tube surfaces that are not joined together are not heated. Thus, in one aspect, no unnecessary heating of selected catheter tube portions takes place, such as, but not limited to, the un-bonded portions of the catheter tube surfaces.

The method of manufacturing disclosed herein is beneficial because it can decrease tooling costs involved in making multilumen catheters. Typically, tooling has to be specially made for each type of catheter being produced. In the platen process, for example, a different platen mold has to be used to accommodate catheters of different French sizes or lengths. In contrast, in the manufacturing process described herein, a one-size-fits-all assembly can be used for many different catheter sizes. In the manufacturing process described herein, one assembly or machine set-up is needed to produce a plurality of different catheter designs. Thus, in one aspect, the manufacturing process described herein is a universal process that can be used to produce catheters of different types.

The heat-bonding process described herein can reduce manufacturing time, increase process controllability, produce a stronger bond compared to chemical or solvent bonding processes, and allows for increased reliability and bonding strength based on changes made in parameters such as heat and pressure. The disclosed process also allows the user to adjust how and where heat is to be applied to at least a portion of the surfaces of the catheter tubes, which allows the user to have the potential to vary the outcome and produce different types of catheter shafts and lumen configurations, including splittable or peelable catheter shafts. The manufacturing process described herein allows separate catheter tubes to be joined into whatever variation or configuration that is desired, and it allows multiple tubes to be intermittently joined to allow for easy perforation or embedded markers, as described above. This process also allows the use of one die which is capable of joining more than one size catheter instead of having to use a different size die for each catheter shape or configuration desired.

The heat-bonding process disclosed herein is beneficial in that it allows the surface of the catheter shaft to remain smooth in contrast to the potentially undesirable outer catheter shaft surface that is produced as a result of the catheter shaft being formed in platen mold processes, which can cause a catheter to take on at least one characteristic of the platen mold finish. Furthermore, with the disclosed process, a clear seam can be created at the outer edge of the at least two catheter tubes 5, 7 when the two catheter tubes 5, 7 are sealed together, as illustrated in FIG. 2A, for example, to indicate to the user or manufacturer the location of the two catheter lumens. This is in contrast to the platen process or any other prior art processes, as described above, in which it can be difficult or impossible to see whether the at least two catheter tubes 5, 7 are joined together without a sleeve or other similar device.

The manufacturing process disclosed herein allows different materials to be used because the catheter tubes are pressurized, and therefore the material that is used during the manufacturing process is not relevant to the process and will not affect the process. The heat-bonding method disclosed herein is beneficial over the chemical and solvent bonding processes described above. The heat-bonding manufacturing process disclosed herein to bond at least a portion of two catheter tubes together is a cleaner, more cost effective, and faster way to bond two catheter tubes together, as described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". The words "including" and "having," as used herein including the claims, shall have the same meaning as the word "comprising." Those familiar with the art can recognize other equivalents to the specific embodiments described herein, which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions can be provided by alternative embodiments without departing from the scope of the appended claims. In this regard, for example, different combinations of elements and/or functions than those explicitly described above are also contemplated as can be set forth in some of the appended claims.

This completes the description of the selected embodiments of the invention. Those skilled in the art can recognize other equivalents to the specific embodiments described herein which equivalents are intended to be encompassed by the claims attached hereto.

What is claimed is:

1. A method of making a multilumen catheter assembly, comprising:
    providing a plurality of tubes, each tube having a first end, a second end, at least one lumen extending longitudinally through at least a portion of each tube, an inner surface and an outer surface;
    selectively heating by contact a first portion of a first tube, wherein the heating consists of heating a first inner surface of the first portion; and
    contacting the selectively heated portion of the inner surface of the first tube with at least a second portion of a second tube, the second portion consisting of a second inner surface, to form a multilumen catheter shaft that is joined together along at least a portion of the length of the catheter shaft.

2. The method of claim 1, wherein the method further comprises:
    simultaneously applying heat to the first and second portions.

3. The method of claim 1, wherein the method further comprises providing at least one tube having a substantially D-shaped cross-sectional lumen profile.

4. The method of claim 1, wherein the method further comprises providing at least one sealing means and sealing at least a portion of the first end of the first tube and the first end of the second tube.

5. The method of claim 4, wherein the method further comprises sealing at least a portion of the second end of the first tube and the second end of the second tube.

6. The method of claim 1, wherein the method further comprises providing tube holding means.

7. The method of claim 6, wherein the method further comprises placing at least a portion of the first tube and a portion of the second tube within a portion of the tube holding means.

8. The method of claim 7, wherein the method further comprises juxtaposing a portion of the first tube with a portion of the second tube to establish contact between a portion of the inner surface of the first tube and a portion of the inner surface of the second tube.

9. The method of claim 1, wherein the method further comprises connecting at least a portion of the first tube and at least a portion of the second tube to at least one pressure source.

10. The method of claim 9, wherein the method further comprises pressurizing at least one lumen of the plurality of tubes.

11. The method of claim 8, wherein the method further comprises providing a tube joining assembly and placing at least a portion of the tube holding means within at least a portion of the tube joining assembly.

12. The method of claim 1, wherein the method further comprises providing at least one heating means, wherein the heating means comprises an outer heating surface and at least one receiving means.

13. The method of claim 12, wherein the method further comprises contacting at least a portion of the first tube inner surface and a portion of the second tube inner surface with a portion of the outer heating surface of the heating means.

14. The method of claim 1, wherein the method further comprises compressing at least a portion of the first inner surface of the first tube with at least a portion of the second inner surface of the second tube.

15. The method of claim 1, wherein the method further comprises bonding at least a portion of the first inner surface of the first tube to at least a portion of the second inner surface of the second tube.

16. The method of claim 1, wherein the method further comprises selectively altering at least one parameter.

17. The method of claim 16, wherein the parameter is selected from the group comprising: temperature, draw speed, air pressure, die pressure, heating means shape, tube holding means shape, tube color, and tube material.

18. The method of claim 1, wherein the method further comprises cooling the plurality of tubes.

19. The method of claim 1, wherein the method further comprises, wherein the multilumen shaft is a unitary shaft along at least a portion of the length of the catheter shaft.

20. The method of claim 1, wherein the method further comprises forming a multilumen catheter shaft having a proximal end and a distal end, wherein a portion of the plurality of tubes at the distal end are capable of independent movement relative to each other.

21. The method of claim 1, wherein the method further comprises forming a multilumen catheter shaft that is joined together along substantially the entire length of the catheter shaft.

22. The method of claim 12, wherein the method further comprises providing at least one additive and feeding the at least one additive through at least a portion of the receiving means, such that the at least one additive becomes embedded within a portion of at least one of the plurality of tubes.

23. The method of claim 22, wherein the additive is selected from the group comprising: at least one wire, at least one electrode, and radiopaque material.

24. The method of claim 1, wherein the method further comprises rotating the plurality of catheter tubes together to form a spiral shaped catheter shaft.

25. The method of claim 1, wherein the method further comprises providing least one mandrel, positioning the mandrel between the first catheter tube and the second catheter tube, and forming a catheter shaft comprising a first lumen, a second lumen, and a third lumen, wherein the third lumen is defined between first lumen and the second lumen.

26. The method of claim 1, wherein the method further comprises forming a catheter shaft that comprises at least a first lumen, a second lumen, and a third lumen, wherein the third lumen is defined between the first lumen and the second lumen.

27. A method of making a multilumen catheter comprising:
providing a plurality of tubes, each tube having a first end, a second end, at least one lumen extending longitudinally through at least a portion of each tube, a first surface and a second surface;
selectively heating by contact a portion of the first tube, wherein the heating consists of heating a first surface of a first tube; and
contacting at least a portion of the first surface of the first tube with at least a portion of a first surface of a second tube to form a multilumen catheter shaft.

28. The method of claim 27 further comprising:
selectively heating by contact a portion of the second tube consisting of a first surface of the second tube.

29. A method of making a multilumen catheter comprising:
providing a plurality of tubes, each tube having a first end, a second end, at least one lumen extending longitudinally through at least a portion of each tube, a first surface and a second surface;
restricting the contact of a heating element to a first surface of a first tube and a first surface of a second tube; and
contacting at least a portion of the first surface of the first tube with at least a portion of the first surface of a second tube to form a multilumen catheter shaft.

* * * * *